US 012048505B2

(12) United States Patent
Thompson et al.

(10) Patent No.: US 12,048,505 B2
(45) Date of Patent: Jul. 30, 2024

(54) MASTER CONTROL DEVICE AND METHODS THEREFOR

(71) Applicant: Intuitive Surgical Operations, Inc., Sunnyvale, CA (US)

(72) Inventors: Allen C. Thompson, Los Altos, CA (US); Grant M. Kadokura, Redwood City, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/206,012

(22) Filed: Jun. 5, 2023

(65) Prior Publication Data
US 2023/0301738 A1 Sep. 28, 2023

Related U.S. Application Data

(63) Continuation of application No. 16/764,346, filed as application No. PCT/US2018/061143 on Nov. 14, 2018, now Pat. No. 11,712,314.
(Continued)

(51) Int. Cl.
A61B 34/00 (2016.01)
A61B 34/20 (2016.01)
(Continued)

(52) U.S. Cl.
CPC .............. *A61B 34/74* (2016.02); *A61B 34/20* (2016.02); *A61B 34/35* (2016.02); *A61B 34/37* (2016.02);
(Continued)

(58) Field of Classification Search
None
See application file for complete search history.

(56) References Cited

U.S. PATENT DOCUMENTS 3,350,956 A   11/1967 Barton et al.
5,176,696 A   1/1993 Saunders
(Continued)

FOREIGN PATENT DOCUMENTS

EP   3015081 A1   5/2016
EP   3245975 A1   11/2017
(Continued)

OTHER PUBLICATIONS

Extended European Search Report for Application No. EP18878247.8 mailed on Jul. 9, 2021, 10 pages.
(Continued)

*Primary Examiner* — Scott Luan
(74) *Attorney, Agent, or Firm* — IP Spring

(57) ABSTRACT

Implementations relate to a master control device. In some implementations, a master control device includes a control body comprising a proximal end, a thumb grip portion, and a finger grip portion. The control body has a length configured to engage the proximal end of the control body in the palm of a hand of the user while the hand engages the thumb grip portion with a thumb of the hand and the finger grip portion with a finger of the hand. The control body is configured to allow the proximal end of the control body to be selectively engaged by the palm of the hand and selectively disengaged from the palm of the hand while the hand engages the thumb grip portion with the thumb of the hand and the finger grip portion with the finger of the hand.

20 Claims, 14 Drawing Sheets

Related U.S. Application Data

(60) Provisional application No. 62/586,752, filed on Nov. 15, 2017.

(51) Int. Cl.
  *A61B 34/35* (2016.01)
  *A61B 34/37* (2016.01)
  *A61B 17/00* (2006.01)

(52) U.S. Cl.
  CPC .............. *A61B 2017/00203* (2013.01); *A61B 2017/00207* (2013.01); *A61B 2017/00216* (2013.01); *A61B 2017/00424* (2013.01); *A61B 2017/00438* (2013.01); *A61B 2017/00973* (2013.01); *A61B 2034/2048* (2016.02); *A61B 2034/2051* (2016.02); *A61B 2034/2055* (2016.02); *A61B 2034/2061* (2016.02); *A61B 2034/2063* (2016.02); *A61B 2034/741* (2016.02); *A61B 2034/742* (2016.02)

(56) References Cited

U.S. PATENT DOCUMENTS

| | | |
|---|---|---|
| 5,876,325 A | 3/1999 | Mizuno et al. |
| 5,976,121 A | 11/1999 | Matern et al. |
| 8,016,818 B2 | 9/2011 | Ellis et al. |
| 8,521,331 B2 | 8/2013 | Itkowitz |
| 8,638,057 B2 | 1/2014 | Goldberg et al. |
| 2008/0262538 A1 | 10/2008 | Danitz et al. |
| 2009/0030428 A1 | 1/2009 | Omori et al. |
| 2010/0069940 A1 | 3/2010 | Miller et al. |
| 2010/0080669 A1 | 4/2010 | Labonville et al. |
| 2010/0228156 A1 | 9/2010 | Valero-Cuevas et al. |
| 2011/0118753 A1 | 5/2011 | Itkowitz et al. |
| 2012/0041595 A1 | 2/2012 | Greeley et al. |
| 2013/0035697 A1 | 2/2013 | Ogawa et al. |
| 2014/0018960 A1 | 1/2014 | Itkowitz |
| 2014/0160015 A1 | 6/2014 | Ogawa et al. |
| 2014/0165770 A1 | 6/2014 | Abri et al. |
| 2014/0276646 A1 | 9/2014 | Wong et al. |
| 2015/0073340 A1 | 3/2015 | Pacheco et al. |
| 2015/0290814 A1 | 10/2015 | Schiele et al. |
| 2016/0202134 A1 | 7/2016 | Malackowski et al. |
| 2016/0216167 A1 | 7/2016 | Blumenkranz et al. |
| 2017/0095298 A1 | 4/2017 | Vakharia et al. |
| 2017/0296280 A1 | 10/2017 | Ogawa et al. |
| 2020/0275985 A1 | 9/2020 | Thompson et al. |
| 2020/0390510 A1 | 12/2020 | Thompson et al. |
| 2021/0298855 A1 | 9/2021 | Thompson et al. |

FOREIGN PATENT DOCUMENTS

| | | |
|---|---|---|
| JP | 2006321027 A | 11/2006 |
| WO | WO-2012127404 A2 | 9/2012 |
| WO | WO-2013018933 A1 | 2/2013 |
| WO | WO-2016154173 A1 | 9/2016 |
| WO | WO-2016201544 A1 | 12/2016 |
| WO | WO-2017031132 A1 | 2/2017 |
| WO | WO-2019099504 A1 | 5/2019 |
| WO | WO-2019099584 A1 | 5/2019 |
| WO | WO-2019217882 A1 | 11/2019 |

OTHER PUBLICATIONS

Extended European Search Report for Application No. EP18879759.1, mailed on Nov. 11, 2021, 13 pages.
International Preliminary Report on Patentability for Application No. PCT/US2018/061031, mailed on May 19, 2020, 13 pages.
International Preliminary Report on Patentability for Application No. PCT/US2018/061143, mailed on May 28, 2020, 15 pages.
International Preliminary Report on Patentability for Application No. PCT/US2019/031813, mailed on Nov. 26, 2020, 10 pages.
International Search Report and Written Opinion for Application No. PCT/US2018/061031, mailed on Apr. 15, 2019, 19 pages (ISRG10290/PCT).
International Search Report and Written Opinion for Application No. PCT/US2018/061143, mailed on Apr. 15, 2019, 22 pages (ISRG09590/PCT).
International Search Report and Written Opinion for Application No. PCT/US2019/031813, mailed on Aug. 14, 2019, 13 pages (ISRG10300/PCT).
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

MASTER CONTROL DEVICE AND METHODS THEREFOR

CROSS-REFERENCE TO RELATED APPLICATIONS

The present application is a continuation of U.S. patent application Ser. No. 16/764,346, filed on May 14, 2020 and titled "Master Control Device and Methods Therefor," which is a U.S. National Phase application of International Patent Application No. PCT/US2018/061143, filed Nov. 14, 2018 and titled "Master Control Device and Methods Therefor," which claims priority to U.S. Provisional Patent Application No. 62/586,752, filed Nov. 15, 2017 and titled "Master Control Device and Method Therefor," the entire contents of both of which are hereby incorporated by reference.

BACKGROUND

In teleoperated operations such as teleoperated surgery, a user typically operates a master controller, e.g., included in a workstation or console, to remotely control (e.g., teleoperate) the motion and functions of instruments at a work site (e.g., surgical site). The master controller utilizes master controls, which will typically include one or more hand input devices such as pincher grips, joysticks, exo-skeletal gloves, or the like. These hand input devices are in communication with the controlled instrument. More specifically, a manipulator or "slave" device including the instrument is moved based on the user's manipulation of the hand input devices. In some examples of a surgical or other medical operation, a hand input device may control, via the teleoperated surgery system, a variety of surgical instruments such as tissue graspers, needle drivers, electrosurgical cautery probes, cameras, etc. Each of these instruments performs functions for the surgeon, for example, holding or driving a needle, grasping a blood vessel, or dissecting, cauterizing, or coagulating tissue.

For some hand input devices, the user may have difficulty manipulating a hand input device while maintaining a secure grip on the hand input device. Further, in some situations, it may be beneficial to operate the hand input device without being bound to a stationary workstation or console.

SUMMARY

Implementations of the present application relate to a master control device and methods for using such a control device. In some implementations, a master control device includes a control body comprising a proximal end, a thumb grip portion coupled to the control body, and a finger grip portion coupled to the control body. The control body has a length configured to engage the proximal end of the control body in the palm of a hand of the user while the hand engages the thumb grip portion with a thumb of the hand and the finger grip portion with a finger of the hand. The control body is configured to allow the proximal end of the control body to be selectively engaged by the palm of the hand and selectively disengaged from the palm of the hand while the hand engages the thumb grip portion with the thumb of the hand and the finger grip portion with the finger of the hand.

Various implementations and examples of the master control device are described. For example, in some implementations, the master control device is a surgical system master control device configured to provide control signals to a surgical teleoperated system. In some implementations, the master control device includes a sensor configured to detect at least one of a position and an orientation of the master control device in a working environment of the master control device. In some implementations, the thumb grip portion includes a thumb grip member rotatably coupled to the control body, and the finger grip portion includes a finger grip member rotatably coupled to the control body. In various implementations, the master control device is mechanically ungrounded, or the control body is coupled to a mechanically grounded linkage.

In various implementations, the proximal end includes an extension member that is rotatable about a longitudinal axis of the control body independently of the control body, the thumb grip portion, and the finger grip portion, and the master control device further includes a tethered connection coupling the control body to a master control system, where the tethered connection extends from the extension member radially from a central axis of the control body, allowing a connection point between the tethered connection and the extension member to rotate with respect to the control body. In some implementations, the master control device includes a wireless transmitter configured to send wireless signals to a master control system based on motion of the thumb grip portion and the finger grip portion (and/or manipulation of input controls).

In some implementations, the control body is configured to allow the proximal end of the control body to be moved by manipulation of the thumb and the finger of the hand on the control body to move the proximal end of the control body into selective engagement with the palm. In some implementations, the control body is configured to allow the proximal end of the control body to be moved between the thumb of the hand and an index finger of the hand while the hand engages the thumb grip portion with the thumb of the hand and the finger grip portion with the finger of the hand.

In some implementations, the control body has a shape configured to engage the proximal end of the control body in the palm of a hand of the user while the hand pinches the thumb grip portion with a thumb of the hand and the finger grip portion with a finger of the hand. In some examples, the proximal end includes an extension member that includes at least a portion of a spherical surface. In various implementations, the proximal end has an axisymmetric shape with respect to the longitudinal axis of the control body, or has an asymmetric shape with respect to the longitudinal axis of the control body. In some examples, the proximal end includes an extension member that extends asymmetrically to one side of a longitudinal axis of the control body, where the extension member is receptive to grasping by a portion of the hand and/or one or more fingers during operation of the master control device. In further examples, the extension member includes a finger aperture receptive to the finger of the hand.

In some implementations, the proximal end includes an extension member that is rotatable about a longitudinal axis of the control body independently of the control body, the thumb grip portion, and the finger grip portion. In some implementations, the finger grip portion is configured to be receptive to at least one of a first finger, a second finger, and a third finger of the hand, and the proximal end is configured to be receptive to at least one of the third finger, a fourth finger, and a fifth finger of the hand.

In some implementations, the proximal end includes an extension member that is translatable along a longitudinal axis of the control body independently of the control body, the thumb grip portion, and the finger grip portion. In some implementations, the proximal end includes an extension member, and the master control device further includes a switch including a ring centered on a longitudinal axis of the control body and positioned between the extension member and the control body, where the ring is linearly translatable with respect to the extension member and with respect to the control body to activate the switch.

Some implementations further comprise an input control coupled to the proximal end and configured to detect a threshold amount of contact with a finger of the hand. In some examples, the input control is coupled to a portion of the proximal end extending asymmetrically to one side of a longitudinal axis of the control body. Some implementations further include a first sensor and a second sensor, the first sensor is coupled to the proximal end and the second sensor coupled to a different portion of the master control device, where the first sensor and second sensor are configured to sense different portions of the hand, e.g., to sense a particular grasping configuration of the hand with the master control device. In some implementations, a distal weighted element positioned at the distal end of the control body and a proximal weighted element positioned at the proximal end of the control body are weighted to provide a center of gravity between a respective finger contact surface of the thumb grip portion and the finger grip portion.

A master control system includes a master device that includes a control body comprising a proximal end, a thumb grip portion coupled to the control body, and a finger grip portion coupled to the control body. The control body has a length configured to, in a first position, engage the proximal end of the control body in the palm of a hand of the user while the hand engages the thumb grip portion with a thumb of the hand and the finger grip portion with a finger of the hand. The control body is configured to allow the proximal end of the control body to be selectively moved to a second position that is disengaged from the palm of the hand, while the hand engages the thumb grip portion with the thumb of the hand and the finger grip portion with the finger of the hand. The system also includes a controller coupled to a slave device and in communication with the master device, where the controller is configured to provide control signals to the slave surgical device while a master-slave control relationship is provided between the master device and the slave device.

Various implementations and examples of the system are described. For example, in some implementations, the master control system is a surgical master control system, and the slave device is a surgical slave device including a surgical instrument. In some implementations, the master control system is configured to maintain the master-slave control relationship while the user performs a first movement of the master device from the first position to the second position. In some implementations, the control body is configured to allow the proximal end of the control body to be moved to the second position that is between the thumb of the hand and an index finger of the hand, while the hand engages the thumb grip portion with the thumb of the hand and the finger grip portion with the finger of the hand. In some implementations, the control body has a shape configured to engage (e.g., ground) the proximal end of the control body in the palm of a hand of the user while the hand pinches the thumb grip portion with a thumb of the hand and the finger grip portion with a finger of the hand.

In various implementations, the proximal end includes an extension member that has an axisymmetric shape with respect to a longitudinal axis of the control body, or that has an asymmetric shape with respect to the longitudinal axis of the control body. In various examples, the extension member can include a finger aperture receptive to a finger of the hand. Some implementations include an extension member that is rotatable about a longitudinal axis of the control body independently of the control body, the thumb grip portion, and the finger grip portion.

In some examples, the proximal end includes an extension member, and the master control system further includes a switch including a ring centered on a longitudinal axis of the control body and positioned between the extension member and the control body, where the ring is linearly translatable with respect to the extension member and with respect to the control body to activate the switch. In some implementations, an input control is coupled to a portion of the proximal end extending asymmetrically to one side of a longitudinal axis of the control body. The master device can be mechanically ungrounded or can be mechanically grounded.

In some implementations, a method of operating a teleoperated system includes establishing a master-slave control relationship between a master device and a slave instrument. The master device comprises a control body having a proximal end, a thumb grip portion, and a finger grip portion. The method includes maintaining the control relationship while the user performs a first movement of the master device. The first movement includes moving the master device from a first position in which the proximal end of the control body is engaged in the palm of a hand of the user while engaging the thumb grip portion with the thumb of the hand and the finger grip portion with a finger of the hand, to a second position in which the proximal end of the control body is moved and disengaged from the palm of the hand of the user while engaging the thumb grip portion with the thumb of the hand and the finger grip portion with the finger of the hand.

Various implementations and examples of the method are described. For example, in some implementations, the first movement includes moving the master device to the second position such that the proximal end of the control body passes between the thumb of the hand and the index finger of the hand while engaging the thumb grip portion with the thumb of the hand and the finger grip portion with the finger of the hand. In some implementations, the method further includes maintaining the control relationship while the user performs a second movement of the master device, where the second movement comprises moving the master device from the second position to the first position. In some implementations, maintaining the control relationship includes sensing the moving of the master device from the first position to the second position with a sensor, and causing output of control signals indicative of the moving of the master device. The control signals cause movement of the slave instrument based on the moving of the master device from the first position to the second position. In some implementations, the proximal end includes a first sensor and a different portion of the master device includes a second sensor, and further comprising sensing a presence of the hand relative to the master device by both the first sensor and the second sensor, wherein establishing the master-slave control relationship is performed in response to sensing the presence of the hand by both the first sensor and the second sensor.

DETAILED DESCRIPTION

Figure 1:
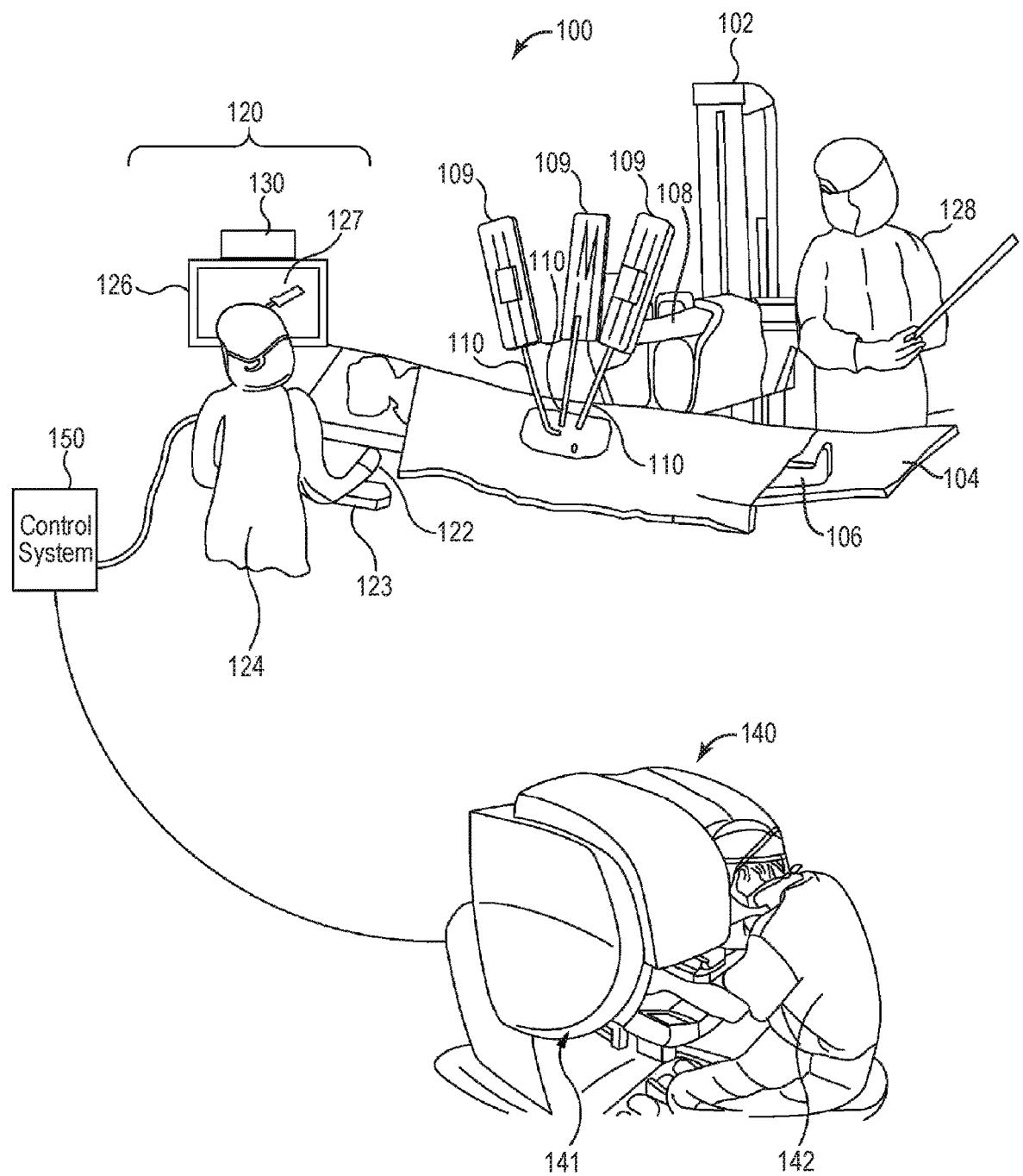
FIG. 1 is a diagrammatic view of an example teleoperated surgical system, according to some implementations.

Implementations relate to a master control device (e.g., a "master hand controller," "master controller," or "hand controller"). As described in more detail herein, implementations provide a master controller enabling user control over multiple functions of a system, such as a teleoperated system (e.g., teleoperated surgical system). The master controller can be adapted to mechanically ungrounded operation by a user in a standing or sitting position, e.g., close to a patient or other site of operations. In some implementations, the master controller may be used in mechanically grounded operation. Functions activated at the activation positions can include functions of surgical tools and other instruments used in treating patients, including instruments used in teleoperated systems.

Described features of the master controller include a proximal end of the controller that is configured to allow a user to manipulate the master controller including engaging (e.g., pinching) a thumb grip portion and finger grip portion with the user's thumb and other finger while the proximal end is engaged (e.g., grounded) in the palm of the user. The control body is configured to allow the proximal end of the control body to be selectively engaged by the palm of the hand and selectively disengaged from the palm of the hand. For example, the controller manipulation is enabled while the proximal end is moved out of engagement with the palm, e.g., moved between the thumb and finger of the hand. Such features allow the master controller to be moved and oriented in space with reduced restrictions to movement while enabling the user to grasp and contact the controller more securely and causing less fatigue, thus reducing inadvertent slippage or dropping of the controller by the user.

Various described features of the master controller include an extension member at the proximal end of the master controller that rotates in one or more directions with respect to the other portions of the master controller to enable more flexible manipulation of the master controller in space. Features include different shapes and sizes of the extension member that enable different amounts and/or types of engagement with the user's hand and fingers. Customization of the extension member can provide different lengths and shapes of the proximal end of the master controller. Input controls can be provided on the extension member to enable the user to activate the input controls to activate associated functions of the teleoperated system.

Described features provide various benefits. For example, a mechanically ungrounded hand controller described herein can be provided with control over operation and functions of a slave device, such as a surgical slave device. Users such as surgeons or other operators may use master controllers over long periods of time during control procedures. Mechanically grounded master controllers may be used in such procedures with reduced fatigue because the grounded connection supports the weight of the controller and may provide gravity compensation. Ungrounded master controllers, however, do not have this grounded connection, and thus an operator may become more fatigued in use of the controller over the duration of a surgical procedure. Furthermore, some ungrounded master controllers may have tethered connections (cables, etc.) that obstruct movement of or add weight to the controller. In addition, ungrounded master controllers (or their tethered connections) may sometimes be knocked or otherwise impacted by the operator's other hand, another person, etc. These factors may cause an ungrounded master controller to slip in the hand of the user or drop out of the hand, which may cause inadvertent and dangerous movements of a controlled slave device. Furthermore, some mechanically grounded master controllers may have similar or other issues with slippage out of an operating hand, e.g., due to blocking structures within the working environment, unexpected collisions with objects, forces applied to the master controller, etc.

Features described herein provide accurate, secure, and safe manipulation of system functions using a master controller. Features such as an extension member at the proximal end of the hand controller provide additional security and reduced fatigue in operating the master controller to reduce incidences of inadvertent slippage or dropping of the controller by the user during controller operation. For example, the extension member is provided at a particular length and/or shape and with a particular surface that allow the proximal end of the controller to be readily grasped and contacted by the palm of the user's hand. For example, the extension member can be grasped by fingers of the user if finger grips of the controller fall from of the user's fingers. Described features also allow the controller to have large fingertip range of motion to provide accurate and precise control over slave instruments, without significantly restricting the range of controller motion. In some implementations, a user can utilize a larger portion of their hand in grasping the master controller, e.g., by using additional fingers to contact the controller in addition to two fingers contacting pincher grips, and/or by using a palm of the hand to engage the controller at particular times. Features such as the length, shape, grips, input controls, and other features of an extension member of the controller enable additional grasping security and enhanced manipulation of the controller. The described features that increase grasping security, reduce fatigue, and increase accuracy of control of the controller are of high importance in procedures where accuracy and consistency in instrument control are required, e.g., medical procedures in which controlled surgical instruments operate on a live patient.

Various terms including "linear," "center," "parallel," "perpendicular," "aligned," or particular measurements or other units as used herein can be approximate, need not be exact, and can include typical engineering tolerances.

Some implementations herein may relate to various instruments and portions of instruments in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As used herein, a mechanically ungrounded master control device refers to a master controller that is unconstrained with respect to possible position and orientation motion in a large working environment (e.g., an operating area or room) and is kinematically separated from the ground, e.g., not mechanically supported by a console, supports, or other object attached to the ground. In some implementations, a mechanically ungrounded master control device may be in tethered or untethered connection with one or more associated components such as control processors, data sources, sensors, power supplies, etc. For example, the master control device may be tethered, e.g., connected physically to these components via a cable or wire, or untethered, e.g., not physically connected to such components and in communication with the components via wireless communication signals.

Aspects of this invention augment the control capability of a computer-assisted teleoperated system through the use of one or more master controllers (e.g., one, two, three, or more) for providing instrument control in various procedures (surgical, procedures in extreme environments, or other procedures), instruction, supervision, proctoring, and other feedback to a user of the system. In some example implementations, master controllers may provide control of one or more of the operational surgical tools in the surgical environment or proxy surgical tools in a virtual environment. One example of a medical device system that may incorporate one or more of these master controllers (e.g., mechanically ungrounded or mechanically grounded) is the da Vinci® minimally invasive teleoperated medical system commercialized by Intuitive Surgical, Inc. of Sunnyvale, Calif.

FIG. 1 is a diagrammatic view of an example teleoperated surgical system 100, including one or more master control devices, according to some implementations.

Figure 20:
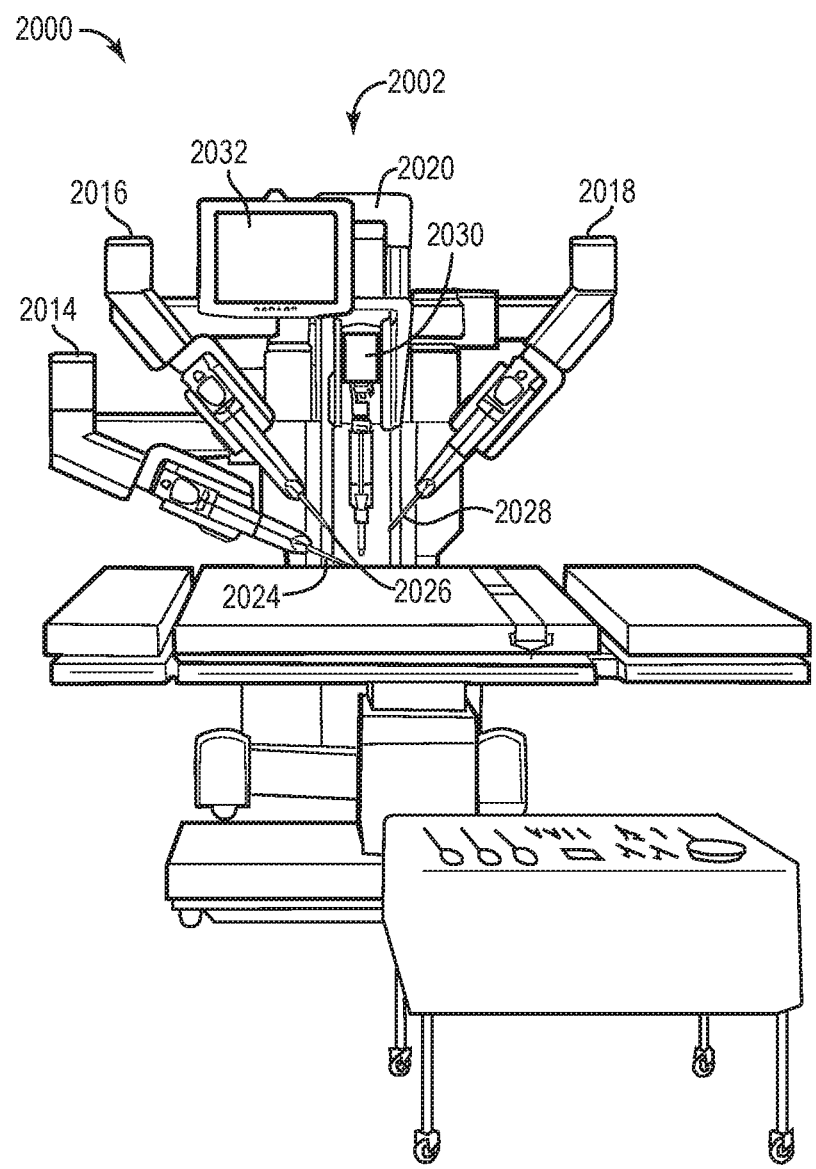
FIG. 20 is a diagrammatic illustration of an example teleoperated slave device and patient site, according to some implementations.

As shown, the teleoperated surgical system 100 generally includes a teleoperated slave device 102 mounted to or near an operating table 104 (e.g., table, bed, or other support) on which a patient 106 is positioned. The teleoperated slave device 102 includes one or more manipulator arms 108, each coupled to an instrument assembly 109. An instrument assembly 109 may include, for example, instruments 110. In some examples, instruments 110 may include surgical instruments or surgical tools. In some implementations, a surgical instrument can include a surgical end effector at its distal end, e.g., for treating tissue of the patient. In various implementations, surgical instruments can include cameras, e.g., cameras for use with surgical procedures. Some examples of an arm assembly for the teleoperated slave device 102 are shown in FIG. 20.

The teleoperated surgical system 100 includes an ungrounded master controller system 120. In this example, master controller system 120 includes one or more mechanically ungrounded master control devices 122 ("master controllers"), some implementations of which are described below, for use by a user 124. The master control device 122 includes at least one mechanically ungrounded, unpowered master tool, e.g., hand controller, contacted or grasped by hand of the user 124. In some implementations, two or more mechanically ungrounded unpowered master tools can be used, e.g., one tool used by each hand of user 124. Example implementations of a master control device 122 are described in more detail below. The master control device 122 can be operated in a sterile surgical field close to patient, as described below. An ergonomic support 123 (e.g., forearm rest) may be provided in the sterile surgical field to support the user's forearms or elbows as the user 124 manipulates master control device 122, e.g., during a surgical procedure.

In some implementations, the slave manipulator arms 108 and/or instrument systems 109 may be controlled to move and articulate the instruments 110 in response to manipulation of master control device 122 by the user 124, so that the user 124 can direct surgical procedures at internal surgical sites through minimally invasive surgical apertures. For example, one or more actuators coupled to the manipulator arms 108 and/or instrument systems 109 may output force to cause links or other portions of the arms 108 and/or instruments 110 to move in particular degrees of freedom in response to control signals received from the master control device 122.

The number of teleoperated surgical instruments 110 used at one time, and/or the number of arms 108 used in slave device 102, may depend on the medical procedure to be performed and the space constraints within the operating room, among other factors. If it is necessary to change one or more of the surgical instruments being used during a procedure, an assistant 128 may remove a surgical instrument no longer being used from its arm 108 or instrument assembly 109 and replace that surgical instrument with another surgical instrument from a tray in the operating room.

Some implementations of the teleoperated surgical system 100 can provide different modes of operation. In some examples, in a non-controlling mode (e.g., safe mode) of the teleoperated surgical system 100, the controlled motion of the teleoperated slave device 102 is disconnected from the master control device 122 in disconnected configuration, such that movement and other manipulation of the master control device 122 does not cause motion of the teleoperated slave device 102. In a controlling mode of the teleoperated system 100 (e.g., following mode), motion of the teleoperated slave device 102 can be controlled by the master control device 122 such that movement and other manipulation of the master control device 122 causes motion of the teleoperated slave device 102, e.g., during a surgical procedure. Some examples of such modes are described in greater detail below.

In this example, user 124 may be a surgeon controlling the movement of instrument systems 108 or a proctor providing supervision and/or instruction for a different surgeon or user (e.g., user 142). Each manipulator arm 108 and the teleoperated instrument assembly 109 controlled by that manipulator may be controllably coupled to and decoupled from mechanically ungrounded master control devices 122. For example, user 124 may sit or stand at the side of patient 106 while working in a sterile surgical field and view display device 126 during a surgical procedure. User 124 performs a medical procedure by manipulating at least master control device 122. In some examples, user 124 grasps master control device 122 in configurations described herein so that targeting and grasping involve intuitive pointing and pinching motions. As the user 124 moves master control device 122, sensed spatial information and sensed orientation information is provided to control system 110 based on the movement of master control device 122.

In some implementations, a hand-tracking transceiver 130 can be included in the ungrounded master controller system 120. For example, hand-tracking transceiver 130 can be positioned to generate a field, for example an electromagnetic field, an optical field (e.g., light beams), etc., in proximity to the user 124. The movement of master control device 122 in this field provides sensed spatial position and orientation information in a three-dimensional coordinate system, e.g., sensed by the transceiver 130 and/or other sensors (e.g., sensors positioned at other locations of the working volume). In some examples, the transceiver 130 can be or include an electromagnetic spatial tracking system, an inertial spatial tracking system, an optical spatial tracking system, a sonic spatial tracking system, etc. The device that senses and outputs sensed information may vary depending on the particular spatial tracking system or combination of tracking systems used. In each implementation, at least sensed position and orientation information for a master control device 122 is provided to a control system 150.

In some implementations, the ungrounded master controller system 120 also includes a display device 126. In some implementations, images captured by one or more cameras of the teleoperated slave device 102 (e.g., on an instrument assembly 109) can be transmitted to the display device 126 and/or transmitted to one or more other displays, e.g., a display coupled to the teleoperated slave device 102 (not shown), a display of the operator input system 140, etc. For example, a surgical environment near or within the patient 106 and the real or virtual instruments controlled by the ungrounded master control device 122 can be displayed by the display device 126 and viewed by the user 122 while the user is operating the ungrounded master controller system 120. Display device 126 can provide a two dimensional image 127 and/or a three-dimensional image 127 of, for example, an end effector of a slave surgical instrument 110 and the surgical site. In some examples, display device 126 provides an output that the user perceives as a three-dimensional image that includes an image 127 of an end effector of a slave surgical instrument 110 and the surgical site. The end effector is located within a sterile surgical field. The three-dimensional image provides three-dimensional depth cues to permit user 124 to assess relative depths of instruments and patient anatomy. The three-dimensional depth cues permit user 124 to use visual feedback to steer the end effector of slave surgical instrument 110 using master control device 122 to precisely target features.

Various embodiments of an ungrounded master control device are disclosed in U.S. Pat. No. 8,521,331 B1 (issued on Aug. 27, 2013, titled "Patient-side Surgeon Interface For a Minimally Invasive, Teleoperated Surgical Instrument"), which is incorporated herein by reference in its entirety.

In some implementations, ungrounded master controller system 120 has at least one component within a sterile surgical field of the surgery. The sterile surgical field is a non-contaminant zone or space near the surgical site in which contaminants are reduced to reduce potential bacterial (or other) contamination to the surgical site during surgery. During surgery, the distal end of at least one teleoperated surgical instrument 110 is positioned within a sterile surgical field. In some implementations, the one or more components in the sterile field can include the master control device(s) 122. For example, master control device 122 is either sterile or draped so that master control device 122 may be safely positioned and used within a sterile surgical field for the surgery. This feature in combination with an image on display device 126 allows a user 124 to control teleoperated slave surgical instruments 110 from within the sterile surgical field. Thus, ungrounded master controller system 120 permits a user 124 to work within the sterile surgical field adjacent a patient 106 undergoing surgery.

Controlling minimally invasive slave surgical instruments 110 from within the sterile surgical field permits minimally invasive surgery combined with direct visualization of patient 106, teleoperated slave device 102, any manually operated surgical instruments, other machines and/or instruments being used in the surgery, etc., by user 124. In some examples, the proximity to patient 106 allows user 124 to control an end effector of teleoperated slave surgical instrument 110 together with one or more manually controlled instruments, such as a laparoscopic instrument or a stapler.

Ungrounded master controller system 120 can reduce operating room floor requirements for the teleoperated surgical system 100. Ungrounded master controller system 120 may provide a lower-cost alternative to a grounded input system 140 (e.g., surgeon's console 141) in a conventional minimally invasive, teleoperated surgical system. For example, ungrounded master controller system 120 can improve safety by allowing user 124, who is performing the operation, to directly observe patient 106 and teleoperated slave device 102 while manipulating instruments 110. System 120 also allows the single user 124 to operate in the sterile surgical field and perform procedures which require coordinated use of manual surgical instruments and one or more teleoperated slave surgical instruments. System 120 promotes collaborative procedures without requiring additional large stand-alone surgeon consoles. In some implementations, assistant 128 may share system 120 to operate other surgical instruments. In addition, multiple users (e.g., surgeons) may collaborate using a common display device 126.

In some implementations, the teleoperated surgical system 100 may also include an grounded input system 140, which allows a second user 142 (e.g., a surgeon or other type of clinician) to view images of or representing the worksite and to control the operation of the manipulator arms 108 and/or the instrument assemblies 109. In some implementations, the grounded input system 140 may be located at a console 141, e.g., a surgeon console, which can be located in the same room as operating table 104. In various implementations, the user 142 can be located in a different room or a completely different building from the patient 106. For example, the surgeon console 141 can be located outside the sterile surgical field.

In this example teleoperated system 100, grounded input system 140 includes one or more mechanically grounded master control device(s) ("master controllers") for controlling the manipulator arms 108 and the instrument assemblies 109. The grounded master controllers may include one or more of any number of a variety of coupled input devices, such as kinematically linked (mechanically ungrounded) hand grips, joysticks, trackballs, data gloves, trigger-guns, hand-operated controllers, voice recognition devices, touch screens, body motion or presence sensors, and the like. In some implementations, the grounded master controllers are provided with the same degrees of freedom as the instruments of the teleoperated assembly to provide the operator with telepresence, the perception that the master controllers are integral with the instruments so that the operator has a strong sense of directly controlling instruments as if present at the worksite. In other implementations, the master controllers may have more or fewer degrees of freedom than the associated instruments and still provide the operator with telepresence. In some implementations, the master controllers are manual input devices which move in all six Cartesian degrees of freedom, and which may also include an actuatable handle for actuating instruments (for example, for closing grasping jaws, applying an electrical potential to an electrode, delivering a medicinal treatment, and the like). Such a grip function is an additional mechanical degree of freedom (i.e., a grip DOF). In some examples, each manipulator arm 108 and the teleoperated instrument system controlled by that manipulator arm may be controllably coupled to and decoupled from the master controllers of input system 140. In some implementations, the grounded master controllers of the input system 140 can include one or more features of hand controllers as described in implementations herein.

The teleoperated surgical system 100 also includes a control system 150. The control system 150 includes at least one memory and at least one processor (not shown), and typically a plurality of processors, for effecting control between the teleoperated slave device 102, the ungrounded master control system 120, and the grounded input system 140. The control system 150 also includes programmed instructions (e.g., a computer-readable medium storing the instructions) to implement some or all of appropriate operations and blocks of methods in accordance with aspects disclosed herein.

For example, control system 150 maps sensed spatial motion data and sensed orientation data describing the master control device 122 in space to a common reference frame. Control system 150 may process the mapped data and generate commands to appropriately position an instrument 110, e.g., an end effector or tip, of teleoperated slave device 102 based on the movement (e.g., change of position and/or orientation) of master control device 122. Control system 150 can use a teleoperation servo control system to translate and to transfer the sensed motion of master control device 122 to an associated arm 108 of the teleoperated slave device 102 through control commands so that user 124 can manipulate the instruments 110 of the teleoperated slave device 102. Control system 150 can similarly generate commands based on activation or manipulation of input controls of the master control device 122 to perform other functions of the slave device 102 and or instruments 110, e.g., move jaws of an instrument end effector, activate a cutting tool or output energy, activate a suction or irrigation function, etc.

While control system 150 is shown as a single block in FIG. 1, the system may include two or more data processing circuits with one portion of the processing optionally being performed on or adjacent the teleoperated slave device 102, another portion of the processing being performed at the ungrounded master controller system 120, another portion of the processing being performed at the grounded input system 140, etc. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 110 supports one or more wireless communication protocols such as Bluetooth, IrDA, HomeRF, IEEE 802.11, DECT, and Wireless Telemetry.

In some implementations, user 124, from within the sterile surgical field, can control at least one proxy visual to a proctor surgeon 142 at surgeon console 141. For example, the proxy visual is visible both in display device 126 and in a display device viewed in surgeon console 141. Using master control device 122, user 124 can manipulate the proxy visual of a surgical instrument to demonstrate control and use of teleoperated slave surgical instruments 110 while user 142 uses master controllers of the surgeon console 141 to control a teleoperated slave instrument 110. Alternatively, second user 142 can control the proxy visual, using a master controller on the surgeon console 141, to instruct user 124. In some implementations, user 124 can telestrate (e.g., draw a freehand sketch over a moving or still video image), or can control a virtual hand or other pointer in the display. In some implementations, user 124 can demonstrate how to manipulate a master tool grip on the surgeon console 140 by manipulating a virtual image of master tool grip that is presented in the displays 126 and on console 140. To facilitate proctoring, a proxy visual module (not shown) of the controller 110 can be processed as part of a vision processing subsystem. For example, the executing module receives position and orientation information, input control states (e.g., switch states, variable slider state, etc.), presence states, grip state, or other information from the master control device 122 and renders stereo images, which are composited with the endoscopic camera images in real time and displayed on any combination of surgeon console 141, display device 126, or any other display systems in the surgical environment.

In some implementations, a controlled teleoperated slave device 102 can be a virtual representation of a device, e.g., presented in a graphical training simulation provided by a computing device coupled to the teleoperated surgical system 100. For example, a user can manipulate master hand controller devices to control a displayed representation of an end effector in virtual space of the simulation, similarly as if the end effector were a physical object coupled to a physical slave device. Some implementations can use master hand controller devices in training, e.g., demonstrate the use of instruments and controls of a workstation including controller devices.

In some implementations, non-teleoperated systems can also use one or more features of the master control devices as described herein. For example, various types of control systems and devices, peripherals, etc. can be used with described master controllers.

Some implementations can include one or more components of a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, California. Features disclosed herein may be implemented in various ways, including teleoperated and, if applicable, non-teleoperated (e.g., locally-controlled) implementations. Implementations on da Vinci® Surgical Systems are merely examples and are not to be considered as limiting the scope of the features disclosed herein. For example, different types of teleoperated systems having slave devices at worksites can make use of actuated controlled features described herein.

Figure 2:
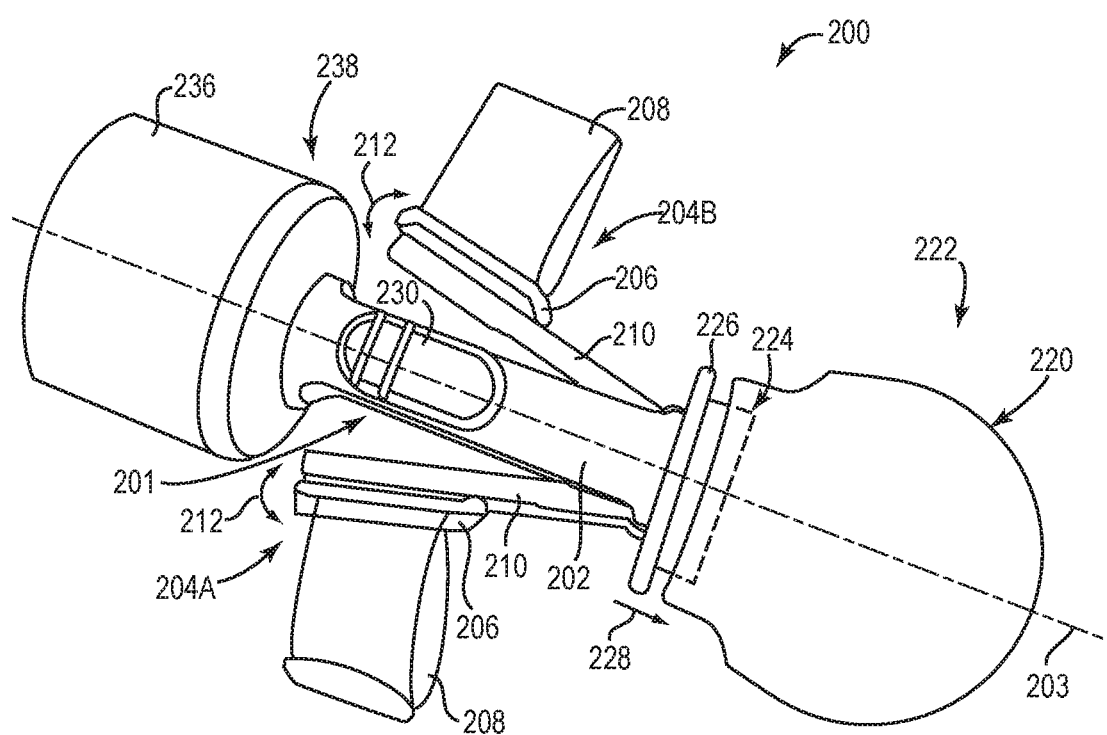
FIG. 2 is a perspective view of an example of a master controller, according to some implementations.

FIG. 2 is a perspective view of an example of a hand controller 200 which can include one or more features described herein, according to some implementations. In some examples, hand controller 200 can be an ungrounded master controller configured to be held by a user's hands and that is mechanically ungrounded during its operation. For example, hand controller 200 can be used as a master control device 122 as described with reference to FIG. 1, or in other master control applications. Hand controller 200 is contacted and held by a user to provide control signals to one or more systems in communication with the hand controller. In this example, hand controller 200 includes a control body 201 and two grip portions 204, labelled as 204A and 204B.

Control body 201 includes a central portion 202 and an extension member 220. Central portion 202 is an elongated member as shown and has a central longitudinal axis 203 along which the central portion extends. The control body 201 can be moved in space and the position and/or orientation of the control body 202 (or another portion of the hand controller 200) in space can be sensed.

One or more sensors can detect, and/or can enable the detection of, the position and orientation of the control body 201 in space, e.g., in a working environment or workspace of the hand controller 200. In implementations where the controller 200 is mechanically ungrounded, the control body 201 is effectively unconstrained for both position and orientation motions within the user's reachable workspace and a sensing workspace. Some examples of sensing systems able to sense the position and orientation of the control body 201 are described above. In some implementations, the control body 201 can include a component that can be tracked by a sensing system that is located externally to the hand controller 200, e.g., one or more magnets, electromagnetic signal emitters, optical patterns, etc. In some implementations, the control body 201 can include a receiving component that receives signals emitted by an external system to assist in determining position and/or orientation of the control body 201 in space. In some implementations, the control body 201 can include one or more sensors or sensor components operative to sense and/or assist an external sensor in detecting position and orientation of the control body 201.

For example, a sensor can track position and/or orientation of the hand controller 200 in a working environment relative to a fixed reference point. In some examples, a sensor Cartesian coordinate system ($X_s$, $Y_s$, $Z_s$) may be generally centered at the sensor. The sensor may serve to track movements, such as the movements of the hand controller 200 and/or user's wrist and forearm, to control a slave device, e.g., rotate and/or translate a surgical tool end effector or other instrument. In some applications, the reference coordinate system may be a finger grip coordinate system, such that any movements measured in the sensor coordinate system may be transformed by an applied transformation from the sensor coordinate system to the finger grip coordinate system. In some examples, motion sensors (accelerometers, gyroscopes, etc.) can be used and provided within the control body 201.

In some implementations, the hand controller 200 does not include a sensor or sensor component for tracking its position and orientation in the workspace, and an external sensor system can perform such tracking (e.g., one or more cameras capturing video and/or motion occurring in the workspace, and a control system detecting and tracking the hand controller in the workspace by examining the captured video or recorded sensor data, etc.).

In some examples, the position, orientation, and/or motion of the hand controller 200 in three-dimensional space can be sensed to control operation of a teleoperated slave device. For example, position, orientation, and motion of the hand controller with respect to a reference position in three-dimensional space can be used to control a corresponding position, orientation, and motion of an arm assembly and/or end effector instrument of a slave device in its available workspace and degrees of freedom.

Grip portions 204A and 204B are coupled to the central portion 202 of the control body 201 (generally referred to as 204). In some implementations, a single grip portion 204 can be provided on the hand controller 200, or more than two grip portions 204 can be provided.

Each grip portion 204A and 204B can each include a grip 206 which is a position or member at which to contact a user's finger. Each grip 206 can have a surface that is shaped to receive a finger pad of the user. In various example implementations, the grip 206 has a contact surface that is flat (e.g., parallel to the grip member portion that extends from the central portion 202), concave (curved inward to form a valley to fit the finger), or convex (curved outward to form a bump or shell engaged by the finger) to provide engagement and secure contact with the fingers of the operating hand. In one example, a convex surface can be suitable in some implementations to make fingertip control of the grips 206 easier, e.g., where the fingertips can roll across the convex surface. The grips 206 can have a tapered surface in some examples. For example, tapered grips can taper inwards, such that the grips are at an angle to the surface of the grip portions to which they are coupled. Some examples of concave and convex grips are described below with respect to FIGS. 11 and 12.

Some implementations can provide protrusions that extend outwardly from the grip 206 in which to cradle a finger, or an aperture in which a finger is inserted. Some implementations of a grip 206 can include texturing such as bumps, ridges, or other patterns of features (some examples described below) to engage the user's finger. A multiple-finger grip 206 can be used in some implementations, where multiple fingers engage a single grip 206. For example, a grip 206 can include adjacent concave depressions (or protrusions forming adjacent spaces that cradle fingers) to engage two or three fingers side-by-side, e.g., the second and third fingers, the third and fourth fingers, or the second, third, and fourth fingers (e.g., with the other grip 206 engaging the thumb).

In some examples, as shown, each grip can include a finger loop 208 which can be used to hold a finger to the associated grip 206. In some examples, a finger loop can include a fastener (e.g., hook and loop fasteners, buckle, etc.) to allow tightening of the loop around the finger. In some implementations, one or more buttons or other controls can be provided on or coupled near to the finger loops 208 (e.g., similar to buttons 1128 of FIG. 12). The two grip members 306 are positioned on opposite sides of a central portion 303 of the handle 302, where the grip members 306 can be grasped, held, or otherwise contacted by a user's fingers. The two finger loops 304 are attached to grip members 306 and can be used to secure a user's fingers to the associated grip members 306. The user may also contact other portions of handle 302 while grasping the grip members 306.

Each grip portion 204A and 204B can also include an associated grip member 210 that is pivotally or rotatably attached to the control body 202 of the hand controller 200 at a pivoting end of the grip member. A grip 206 and finger loop 208 is coupled to a finger end of each associated grip member 206. The grip portion can be moved, e.g., by a user, in an associated degree of freedom 212 with respect to the control body 202, where the finger end of the grip member 210 is moved. Thus the associated grip 206 and finger loop 208 coupled to that finger end are moved with the grip member 210. For example, the grip members 210 can be moved simultaneously in a pincher-type of movement (e.g., toward or away from each other). In some implementations, one of the grip members 210 can be moved in its degree of freedom 212 while the other grip member 210 (or other grip 206) can be fixed with reference to the control body 202. In some implementations, both grips 206 can be fixed with reference to the control body 202, e.g., grips 206 can be coupled directly to the control body 202 or can be coupled to a structure that does not move with respect to the control body 202.

One or more sensors (not shown) coupled to the hand controller 200 can detect the positions of the grip members 210 in their degrees of freedom 212 and send signals describing the positions to one or more control circuits of the system to which the controller 200 is connected, e.g., teleoperated surgical system 100 or other system. For example, optical encoders, potentiometers, or other sensors can be used. In some examples, the control circuits provide control signals to the teleoperated slave device 102, an example of which is described with reference to FIG. 21. For example, the positions of the grip members 210 in degrees of freedom 212 can be used to control jaws or other components, or any of various degrees of freedom, of an end effector of a controlled slave device (e.g., teleoperated slave device 102). In some examples, the two finger grips 206 of hand controller 200 can be moved together or apart by the user in pincher motions to, for example, correspondingly move forceps, pliers, or other instrument end effector of the teleoperated slave device.

In some implementations, one or more springs or other actuators can be provided between each grip member 210 and the control body 202, to provide a resistive force in particular directions of the grips 206 (e.g., movement in directions toward each other in degree of freedom 212.) In some implementations, the actuators can provide a restoring force to the grip member 210 toward an open position of the grip member. When the user reduces finger force on the associated grip 206, the grip member 210 may be moved toward the open position by the restoring force. In various implementations, the resistance and/or restoring force on the grip members can be provided by various types of actuators, e.g., passive actuators that provide a passive resistive force to movement (such as springs that provide an increasing resistive force the closer the grip member is moved to the central portion, or dampers, resistive elements, etc.) and/or active actuators (motors, voice coils, etc.) that provide an active force. In some implementations, the actuator(s) provide forces that are varied based on a control signal provided to the actuator(s) from a controller. In some examples, the grip members can include a power assist mechanism using one or more actuators to provide assistive force to the grip members and assist the user when moving a grip member between positions. In some implementations, other types of forces can be provided on the grip portions 204, e.g., damping force, force pulses or vibrations, etc. In some examples, a sensor and/or actuator can be housed in control body 202 which is coupled to the grip members 210 by a transmission.

The control body 201 of the hand controller 200 also includes an extension member 220 that forms a proximal end 222 of the control body 201. In some implementations, the extension member 220 and the central portion 202 form a unitary control body 201. In some implementations, extension member 220 is coupled to a separate central portion 202. In some implementations, the extension member 220 is removable from the central portion 202 and, for example, can be replaced at the proximal end 222 of the control body 201 by a differently-sized and/or differently-shaped extension member.

In some implementations, at least a portion of the extension member 220 (e.g., the proximal end of the control body) has an outer surface that is spaced further from the longitudinal axis 203 than the outer surfaces of the central portion 202, e.g., the portion of the extension member 220 has a greater radius at its cross-section than the central portion 202. This allows the extension member to be easily contacted or grasped by the user's hand. In the shown implementation, the extension member includes at least a portion of a spherical surface, e.g., a hemispherical surface or a similarly-curved surface at the furthest proximal end of the extension member 220. Other forms, shapes, and features of the extension member can be provided in other implementations. For example, the extension member can have a cylindrical or oblong shape, rectangular or other polygonal faces, rounded corners, etc.

In this example implementation, the extension member 220 (e.g., proximal end of the control body 201) is axisymmetric, e.g., has an symmetric shape with respect to revolution about a longitudinal axis of the control body. In some implementations, the extension member 220 has a shape that is asymmetric with respect to the longitudinal axis 203 of the control body 201, some examples of which are described below. Some implementations can provide a rigid extension member 220 that is not deformable by the user's hand, and other implementations can provide a deformable, compressible, or flexible extension member 220 or a deformable, compressible, or flexible covering to the extension member 200, e.g., made of rubber, foam rubber, neoprene sponge, or other deformable material. Such materials can be used in any of the implementations described herein.

In some implementations, one or more physical connections, e.g., a tether connection such as a cable, may extend out of the extension member 220 to connect the hand controller to a master control system, some examples of which are described below.

During usage of the hand controller 200, the proximal end 222 of the control body 201, e.g., the extension member 220, is typically positioned closer to the palm of the user than the grips 206. The control body 201 has a length and/or shape that is configured to selectively engage or contact (ground) the proximal end of the control body in or against the palm of the hand of the user while the hand engages (e.g., pinches or holds) the thumb grip portion 204 (e.g., grip 206) with a thumb of the hand and the finger grip portion 204 (e.g., grip 206) with a finger of the hand. In some implementations, the extension member 220 is made sufficiently small to allow this selective engagement. For example, during use of the hand controller 200, at least a portion of the curved surface of the extension member 220 can be selectively made to engage (e.g., contact) the user's palm by manipulating the control body 202 and grip members 210 using the portions (e.g., tips) of the user's fingers contacting the grips 206. Engagement with the palm in this context refers to contact between the extension member and the palm, e.g., grounding of the control body to the hand of the user. Disengagement from the palm refers to removing such contact between control body and palm.

Thus, the control body is configured to allow the proximal end 222 (e.g., extension member 220) to be selectively engaged by the palm of the hand and selectively disengaged from the palm of the hand. For example, the control body is configured to allow the proximal end to be moved by manipulation of the thumb and the grip finger of the hand on the control body to move the proximal end into selective engagement with the palm. In some implementations, the control body is configured to allow the proximal end to be selectively moved into engagement with the palm using additional fingers of the hand that are different than the thumb and the finger contacting the grips, e.g., the third, fourth, and/or fifth fingers, as described in greater detail below.

In some examples, the extension member 220 is selectively and naturally cradled or surrounded by the user's palm, without engagement or contact with the palm, while the control body 202 and grip members 210 are manipulated using the user's fingers, such that the extension member 220 can be contacted by the palm of the user when desired or if an unintentional slippage or displacement of the controller 200 occurs in the hand. In this example, the proximal end or extension member provides security because it is in a position to be grasped if additional security is desired or needed. The extension member 220 is naturally cradled near to the hand due to the natural curvature of the additional, non-gripping fingers (e.g., fourth and fifth fingers), so that if the controller slips, the proximal end will contact at least one of the palm, fourth finger, and fifth finger, thus providing added security. For example, at any time, one or more of the non-gripping fingers can contact the extension portion 220 to move the extension portion 220 into engagement with the palm for added security in a grasping motion. These fingers can release their contact with the extension portion 220 to allow disengagement of extension portion 200 and the palm when the user desires to have easier fingertip control of the controller 200.

In addition, the extension member 220 can be pivoted or otherwise moved out from the space adjacent to or contacting the user's palm to allow a greater range of motion of the hand controller when the user changes orientation of the hand controller in space, e.g., using the hand's fingertips. For example, the fingers on grips 206 can act as a fulcrum around which the controller 200 is moved. Thus, the finger tip range of motion of the hand controller is increased by configuring the extension member 220 to allow such motion. For example, the control body 201 is configured to allow the proximal end of the control body 201 (e.g., the extension member 220) to be moved between the thumb of the hand and the first (index) finger of the hand while the hand engages (e.g., pinches or holds) the thumb grip portion (e.g., grip 206) with the thumb of the hand and the finger grip portion (e.g., grip 206) with a finger of the hand. Alternately, the proximal end (extension member 220) can be moved in a direction opposite to the area between the thumb of the hand and an index finger of the hand. Such movement or positioning examples are described in greater detail below with respect to FIGS. 6 and 7. Such fingertip motion can be easier when the control body 201 is provided at a length such that the extension member 220 does not contact the palm of the hand (e.g., is positioned with space or gap between its surface and the palm) while the user is holding the hand controller in a centered position, e.g., a position where the axis 203 approximately passes into/through a center portion of the palm such as the position shown in FIG. 3.

The spherical or curved surface of the extension member 220 allows a user's palm to comfortably contact or manipulate the extension member 220 when desired. This can allow the user to use an increased portion of their hand to manipulate the controller, e.g., in addition to the fingertips that contact the grips 206. This may be more comfortable for users who are more familiar with using larger portions of their hands to manipulate controllers. Furthermore, the extension member 220 can provide increased security against dropping and/or slipping of the hand controller 200 during use by providing a surface that is convenient to contact or grasp by the hand. In addition, the extension member 220 allows better management of holding the hand controller 200 by providing a portion to hold if the user wishes to readjust his or her fingers on the grips 206, e.g., causing fewer inadvertent drops of the hand controller. Furthermore, the extension member 220 at the proximal end of the controller can set the center of gravity of the hand controller 200 further toward the proximal end 22 of the control body 201. For example, this may adjust the center of gravity closer to the grips 206 for more balanced usage, e.g., if other weight exists at the distal end of the hand controller 200.

The ease of moving the hand controller 220 with respect to the operating hand can also be advantageous in implementations providing detected gestures. For example, some implementations can detect different orientations, positions, and/or motions of the hand controller 200 in space as gestures that can be used to activate or command various functions in a teleoperated system (e.g., gesture poses and/or gesture trajectories). For example, a first gesture pose can be to align the control body 202 vertically in space pointing the distal end in one direction, which commands a first function of the system, and a second gesture pose can be to align the control body 202 vertically and pointing in the opposite direction, which commands a second function of the system. Such manipulation can be provided using the hand controller 200 while still retaining the security of grasping the hand controller 200 so that it is not inadvertently dropped and/or does not partially slip out of the hand.

In some implementations, the extension member 220 and central portion 202 are rotatable about the longitudinal axis 203 of the control body 201 with respect to each other. In some examples, the extension member 220 is rotatable about the axis 203 independently of the central portion 202 and grip portions 204A and 204B. In some examples, a rotary coupling is provided between central portion 202 and extension member 220. This rotation can allow the central portion 202 and grip portions 204 to be rotated about the axis 203 with respect to the extension member 220, e.g., by the user's fingers, while the extension member 220 is held engaged to the palm or other portion of the user's hand (e.g., grounded to the hand). Similarly, the extension member 220 can be rotated about the axis 203 with respect to the central portion 202. In some implementations, the extension member 220 can pivot in all axes with respect to the central portion 202, e.g., using a spherical joint or coupling provided between central portion 202 and extension member 220. Some examples of such an implementation are described below with respect to FIG. 15. In some implementations, the rotary position of the extension member about axis 203, and/or the rotation or pivoting motion of the extension member 220 about axis 203, can be sensed using one or more sensors coupled to the central portion 202 and/or extension member. For example, such position or rotation can be used to sense a rotary position of an input control or asymmetrical feature on the extension member, sense a current location of a tethered connection that extends from the extension member 220 (e.g., as in FIG. 5), etc. For example, sensing particular rotary positions or motions can cause the system to output a displayed, audio, and/or haptic indicator or alarm, exit controlling mode, etc. if the current position or motion matches (within a threshold amount) any of the particular positions or motions.

In some implementations, the extension member 220 can be expanded or collapsed in its length or size to allow adjustment in controller size and customization to a particular user's hand. For example, the extension member 220 can have an expandable surface to allow it to be increased in diameter, or can be configured to extend/collapse in a particular direction or along a particular axis (e.g., along an axis parallel to axis 203). In some implementations, the extension member 220 can be removed, e.g., disconnected from central portion 202, e.g., if only fingertip control of the controller 200 is to be used. In some implementations, a differently-sized extension member 220 can be connected to the central portion 202 in place of the removed extension member.

In some implementations, the extension member 220 can be moved or extended linearly, e.g., can be translatable along the longitudinal axis 203 independently of the central portion 202 and the grip portions 204. For example, the extension member 220 can be adjusted along the axis 203 to fit a particular-sized hand of the user, e.g., such that the grips 206 are more comfortable to use by the fingers of the user while the extension member 220 rests against or is positioned near the user's palm. For example, the central portion 202 can include a telescoping portion to allow the extension member 220 to be adjusted parallel to axis 203. In some implementations, detents or other mechanisms can be provided to lock or bias the extension member 220 at particular positions along the axis 203, e.g., such that additional force is required from the user's hand to move the extension member 220 out of these positions.

In some implementations, a sensor can be provided in hand controller 220 to sense the position and/or linear motion of the extension member 220 parallel to the axis 203 and relative to the central portion 202. For example, a linear sensor, mechanical switch, optical encoder, optical sensor, or other type of sensor can be used as the sensor. This sensing can allow a controller (e.g., the control system 150) to determine the distance or amount that the extension member 220 has been moved in a particular direction, and/or to determine a current position of the extension member 220 in its linear range of motion. In some implementations, such a sensor can sense a control signal activation by detecting a threshold amount of translation of the extension member 220 along the longitudinal axis 203. For example, such a sensor can be a switch that is activated in response to the user pressing on the proximal end of the extension member 220 to move it a threshold distance toward the distal end of the hand controller 200. In some implementations, this activation is considered an activation of an input control with similar effect to, e.g., the activation of switch 224 described below.

In some implementations, hand controller 200 can also include one or more input controls (also referred to as an "activation control," "activation control switch," or "activation control button"). An input control includes one or more sensors (e.g., mechanical switches, optical sensors, magnetic sensors, capacitive sensors, pressure sensors, etc.) that detects user input, e.g., the engagement or activation of a user's finger with the input control. Input controls can be used to detect activations of control signals by the user by, e.g., detecting a position of a finger or a threshold amount of contact with a finger of the user's hand. In some examples, an input control is a physical pushbutton or sliding switch that is operative to be activated by user input, e.g., engaged, slid, or pressed downward by at least a portion of a finger of the user that is operating the hand controller 200. Various other types of input controls can be also or alternatively be used to enable user activation of a control signal, e.g., optical sensor areas, capacitive sensor areas, pressure sensors, etc. The activation of an input control causes a control signal to be output by the input control, e.g., to a control system. The control system can be in the housing of the hand controller 200 and/or in a separate device in communication with the hand controller (e.g., as described for control system 150 of FIG. 1). In some examples, the control signal can cause activation of a particular function provided by a system in communication with the input control as described above.

Input controls can be provided at any surface or portions of hand controllers described herein, e.g., on the central portion 202, one or more grip portions 204, extension member 206 (e.g., at the proximal end of the hand controller or on a different portion of the surface of the extension member), etc. An input control can be used to sense user input to cause activation of particular system functions, and/or to sense contact or use of the hand controller by a user.

In the example of FIG. 2, the input controls include an extension member switch 224 provided between the extension member 220 and the central portion 202. Switch 224 includes a ring 226 that can be centered on the central axis 203 of the hand controller. Ring 226 activates (e.g., closes or opens) the switch if the ring is linearly translated by the user with respect to the extension member 220 and central portion 202 along the central (longitudinal) axis 206. For example, pressing ring 226 to move in a direction 228 toward the proximal end 222 of the hand controller 200 can cause switch 224 to close, which causes a control signal to be sent to the control system to trigger an associated function of, e.g., the teleoperated system 100 (e.g., camera mode activation, a clutch control to enter or exit controlling mode, etc.). In some implementations, the switch can be an input control that outputs a variable control signal that is based on a current position of the ring in a linear degree of freedom, where the current position is one of multiple different available positions of the ring, e.g., more than two positions. The extension member 224 is provided in a position allowing easy access to the switch by a variety of fingers of the hand operating the controller 200, and since the ring of the switch extends fully around the controller (around axis 203), switch 224 is accessible on any side of the controller 200 regardless of the particular orientation of the hand controller in space with respect to the user's fingers.

In additional examples of input controls, a finger switch 230 can be provided on the central portion 202 to enable control of one or more functions of the teleoperated system. The finger switch 230 can be a sliding switch as shown (e.g., translatable parallel to the axis 203), or can be a press switch or button, optical sensor area, or other form of switch activatable by a finger. The finger switch 230 can engage a user's finger during operation of the hand controller 200. For example, the finger switch 230 can be engaged by a user's finger that is located between two fingers that operate the finger grips 206. In some examples, a thumb operates one grip 206, a grip finger operates the other grip 206 (e.g., a third and/or fourth finger), and a second (e.g., index) finger between the thumb and grip finger operates the switch 230.

Other switches can be positioned at other portions of the hand controller 200, some examples of which are described below. In some implementations, various types of controls can be provided on the hand controller to provide input signals based on physical manipulation of the controls by the user's hand, such as dials, knobs, buttons, sliders, trackpads or capacitive sensors, joysticks, trackballs, pivoting switches, etc.

In some implementations, the hand controller 200 can include one or more presence sensors that detect that a user's hand is engaged with and/or operating the hand controller 200. For example, optical sensors, pressure sensors, etc. can be used, e.g., at one or more of the grips 204, at the extension member 220, and/or at other areas of the controller 200. For example, the presence sensors can be used to determine whether a user is proximate to and/or operating the hand controller. In some implementations, one or more input controls can be used as presence sensors.

In further example implementations, multiple presence sensors can be provided at various locations of the hand controllers described herein to measure user proximity at multiple locations, e.g., to avoid false positive and/or false negative measurement of particular hand grip configurations of the controller. For example, output signals from a sensor that measures user presence by, e.g., sensing user proximity (such as distance) of the proximal end (e.g., extension member 220) of the controller to the palm can be examined by the system in combination with output signals from a second sensor (and/or third sensor, fourth sensor, etc.) simultaneously measuring user proximity of different portion(s) of the controller to different portion(s) of the user's hand. For example, a second presence sensor can be located at the central portion 202 (e.g., on one side of switch 230 toward the proximal end) and can sense proximity of a central portion 202 of the hand controller to a segment of the index finger or thumb of the user's hand. In another example, a second (or third, etc.) presence sensor can be located on one or more grips 206 or grip members to sense user proximity of tips or other segments of fingers to the sensor. In some implementations, a particular combination of sensing by a plurality of presence sensors of the hand controller that indicates hand engagement of different portions of the users hand to particular portions of the hand controller can be required to activate use of the controller and/or to activate particular controlled functions of the system, e.g., to send a control signal that causes entering a controlling mode or activates other functions. Such combination of sensing can indicate that the user's hand is in a particular grasping configuration with respect to the hand controller. This sensing can provide a higher confidence estimate to the system that the user's hand is in a predetermined or intended grasping configuration when engaged with the hand controller, where portions of the hand are located in predetermined locations with respect to particular portions of the hand controller.

In further examples of presence sensing, one or more input controls can be used as presence sensors to sense presence of the hand with respect to the hand controller and can be used by the system to estimate a user's intent with respect to activating one or more functions of the teleoperated system, e.g., to enter a controlling mode, exit a controlling mode, activate a function of a slave device, etc. For example, a confirmation input control can be provided on the hand controller 200 that, when activated by the user, indicates that the user is ready to activate one or more functions (e.g., enter a controlling mode, activate one or more other particular functions, etc.), and which enables such activation to be performed (e.g., in response to receiving input from one or more other input controls). In some examples, this activation is not enabled prior to activation of the confirmation input control. In some implementations, this activation can be enabled for a particular time period after activation of the confirmation input control. The confirmation input control can be an additional, dedicated input control used for such indication, or can be an input control that is also used for other functions as described herein. In some examples, the confirmation input control can be a button, switch, sensor (e.g., optical or capacitive sensor), or other control on the hand controller that is activated by squeezing the proximal end (e.g., extension member 220) with the palm, or activated with fingers that are not used to actuate a gripper mechanism (e.g., finger(s) that can activate an extension member switch 224, extension buttons 1010, etc., of the proximal end).

In further examples of user presence sensing, a determination that user presence is no longer sensed by one or more presence sensors can be used to activate particular functions. For example, determining that a user has disengaged a hand from the hand controller, as sensed by a particular presence sensor, can cause the system to enter a more-persistent type of non-controlling mode in which explicit command(s) are required to be input by the user for the system to re-enter controlling mode. For example, an explicit command can be provided to the control system via a different input control of the hand controller (e.g., a switch, button, etc.), or a command provided to the control system via a different input device (e.g., a foot pedal or other foot control, a separate sensor that senses the user or a portion of the user such as the user's head, gaze, etc.). In some implementations, sensing user disengagement from the hand controller by a specific presence sensor (e.g., a different presence sensor than sensor(s) associated with the more-persistent controlling mode described above) can cause the system to enter a less-persistent non-controlling mode, from which re-entering controlling mode has fewer or simpler input sensing requirements than for the more-persistent non-controlling mode. For example, such input sensing requirements can include sensing user presence at the same specific presence sensor after such disengagement is sensed (e.g., within a threshold time period after disengagement is sensed).

Some implementations of the hand controller 200 can include a distal element 236 coupled at the distal end 238 of the control body 202, e.g., at the opposite end of the control body 202 to the extension member 220. The distal element 236 can, in some implementations, include one or more sensors or sensor components used for tracking the position and/or orientation of the hand controller 200 in space, e.g., in a working environment such as a surgical environment. For example, receivers, transmitters, motion sensors, and/or other sensor components can be provided in the distal element 236.

Alternatively, these sensor(s) can be positioned at various locations on or in the housing of the hand controller 200, e.g., on the central portion 202 below or above the grip portions 204. In some implementations, the hand controller 200 can include one or more sensors or sensor components operative to sense and/or assist an external sensor in detecting position and orientation of the hand controller 200. For example, motion sensors (accelerometers, gyroscopes, etc.) can be used within the hand controller 200 in some implementations. In various implementations, the sensor may be a six degree of freedom (6 DOF) electromagnetic (EM) sensor, an optical tracking sensor, a fiber optic shape sensor, or another type of sensor.

In some implementations, the sensor may be one component of a sensor system, where additional components of the sensor system are positioned external to the hand controller 200 (e.g., hand-tracking transceiver 130 of FIG. 1). For example, the hand controller 200 can include a component (e.g., sensor 234) that can be tracked by a sensing system that is located externally to the hand controller 200, e.g., a component such as one or more magnets, electromagnetic signal emitters, optical patterns, etc. In some implementations, the hand controller 200 can include a sensor receiving component that receives signals emitted by an external system to assist in determining position and/or orientation of the hand controller 200 in space. In some implementations, the hand controller 200 includes a sensor or sensor component for tracking its position and orientation in the workspace, and an external sensor component can perform such tracking (e.g., one or more cameras capturing video and/or motion occurring in the workspace, and a control system detecting and tracking the hand controller in the workspace by examining the captured video or recorded sensor data, etc.)

In some implementations, the distal end element 236 includes a weighted element to provide a weight on distal end of the control body 202, e.g., to provide a particular weighted balance to the hand controller 200 in coordination with the weight at the proximal end from the extension member 220. These weights can be selected to provide a center of gravity at a particular location or portion of the hand controller 200. In some implementations, a distal weighted element at the distal end of the control body (e.g., a sensor and/or one or more additional weighted elements) and a proximal weighted element at a proximal end of the control body (e.g., extension member 220 and/or one or more additional weighted elements) are weighted to provide a neutral balance to the controller 200, e.g., a balance such that the center of gravity of the controller 200 is in a middle portion of the controller in proximity to the grips 206. In some examples, the center of gravity can be provided in a region of the controller that is on the control body 202 and between (e.g., approximately centered between) the thumb and finger grips 206.

In some implementations, the hand controller 200 may include sensors that provide safeguards against the hand controller 200 inadvertently dropping. For example, in some implementations, the thumb grip 204 and/or the finger grip 214 may include a sensing mechanism (not shown) that senses contract with the fingers of the user. In some implementations, the hand controller may include an accelerometer (not shown) that senses if the hand controller drops, e.g., to the ground. The sensing mechanism and/or the accelerometer may detect if the hand of the user releases the hand controller 200. For safety, the hand controller 200 may then discontinue control of the slave devices of the teleoperated system 100.

In some implementations, one or more tethered connections can be connected to and extend out of the distal end 238 and/or the distal element 236. Various control signals from sensors of the hand controller 200 can be output via the tether connection, and/or various signals from a control system can be received. For example, the tethered connections can be cables that are attached to a control system, e.g., control system 150 of FIG. 1. In some implementations, the tethered connections can extend out of the proximal end of the hand controller, e.g., out of the extension member 220, instead of out of distal end 238, as described in greater detail below. In some implementations hand controller 200 is not tethered by physical connections, and can communicate with the control system via wireless signal communications. For example, a wireless transmitter can be provided in some implementations within the distal element 236, where the transmitter is configured to send wireless signals to a master control system based on position, orientation, and/or motion of the control body 201 in space, based on the thumb grip and the finger grip portions 204 in their degrees of freedom, and/or based on the activations of input controls of the hand controller.

In some implementations, the hand controller 200 can be a mechanically grounded controller. For example, the control body 201 can be coupled to a mechanical linkage that is coupled to the ground, providing a stable platform for the use of the hand controller. For example, the hand controller 200 (or other hand controller implementations herein) can be coupled to a mechanical linkage that is coupled to the ground or an object connected to ground, providing a stable platform for the use of the hand controller 200. For example, the control body 201 of the hand controller 200 can be coupled to a grounded mechanical linkage at the distal end 212 of the hand controller. The mechanical linkage can provide six or more degrees of freedom to the hand controller 200. Some examples of such linkages are described below with reference to FIGS. 17 and 18, and in U.S. Pat. No. 6,714,839 B2, which is incorporated herein by reference.

Figure 3:
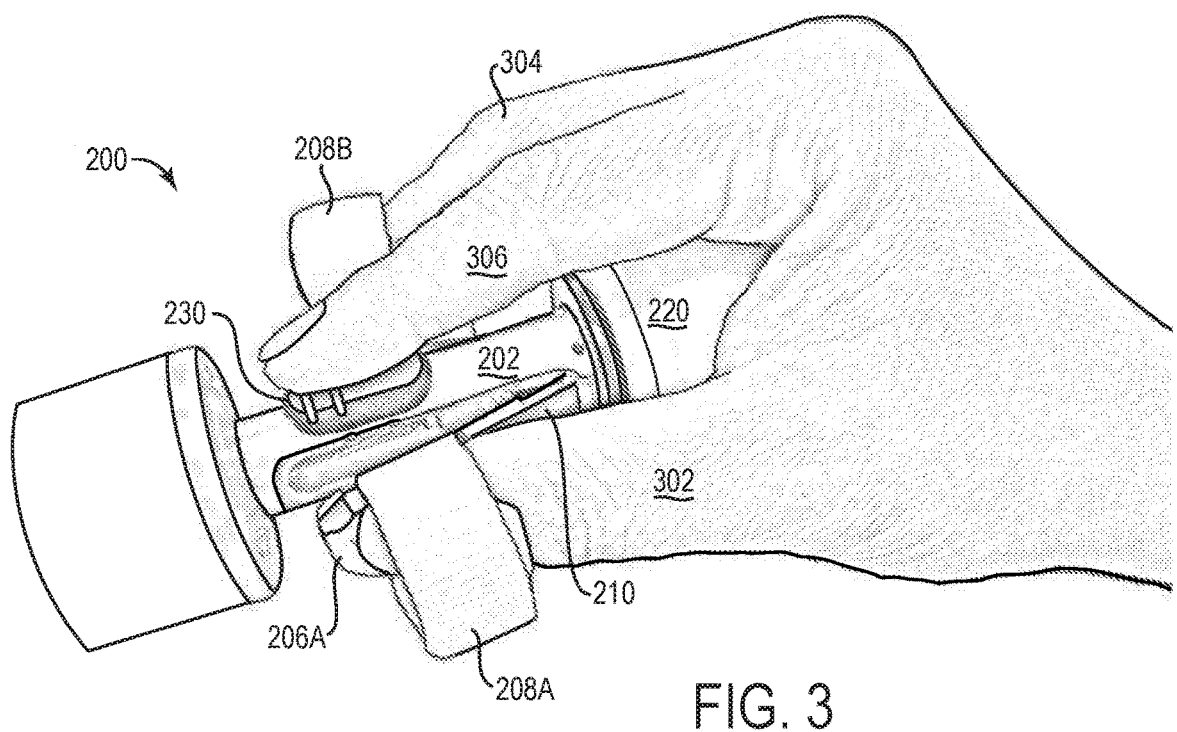
FIG. 3 is a perspective view of the master controller of FIG. 2 being manipulated by a user's hand, according to some implementations.

FIG. 3 is a perspective view of the master hand controller 200 being manipulated by a user's hand, according to some implementations. In this example, the user's thumb 302 is engaged with grip 206A and secured by finger loop 208A. The user's third finger 304 is engaged with grip 206B (not shown; e.g., see FIG. 4) and secured by finger loop 208B. The user's second finger 306 is engaged with the finger switch 230, e.g., to slide the finger switch 230 forward and/or back to different activation positions.

In this example, the extension member 220 is engaged with the user's palm, e.g., contacted by the palm to more reliably grip the hand controller 200 while manipulating the grip portions 204 and finger switch 230 with the user's fingers.

Figure 4:
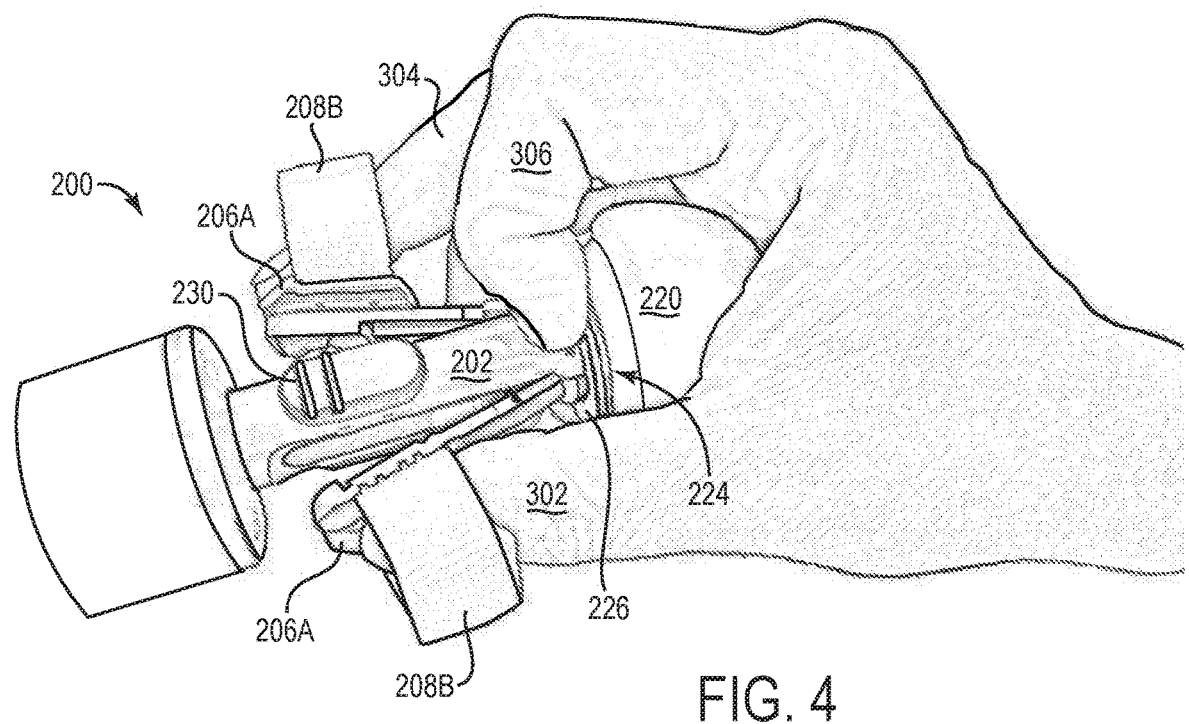
FIG. 4 is a perspective view of the master controller of FIG. 2 being manipulated by a user's hand to activate a switch adjacent to the extension member, according to some implementations.

FIG. 4 is a perspective view of the master hand controller 200 being manipulated by a user's hand to activate a switch adjacent to the extension member, according to some implementations. For example, FIG. 4 can be a preceding or following movement or action by the user's hand relative to the hand position shown in FIG. 3. In the example of FIG. 4, the user has moved the second finger 306 to engage the extension member switch 224 positioned between the control body 202 and the extension member 220. For example, the second finger 306 can be moved toward the extension member 220 to move the ring 226 of the switch 224 toward the palm of the user (e.g., toward the proximal end of the hand controller 200) which activates the switch 224. For example, the ring 226 can receive a restoring force provided by a spring or other actuator, which causes the ring 226 to return to its (unactivated) position if the second finger 306 removes sufficient force that was applied toward the extension member 220.

In some implementations, the ring 226 can also or alternatively be activated using a different finger of the hand of the user. For example, the fourth finger, fifth finger, etc. can engage the ring 226 and move it toward the proximal end of the hand controller 200, e.g., on a side of the controller 200 nearest to those fingers.

Figure 5:
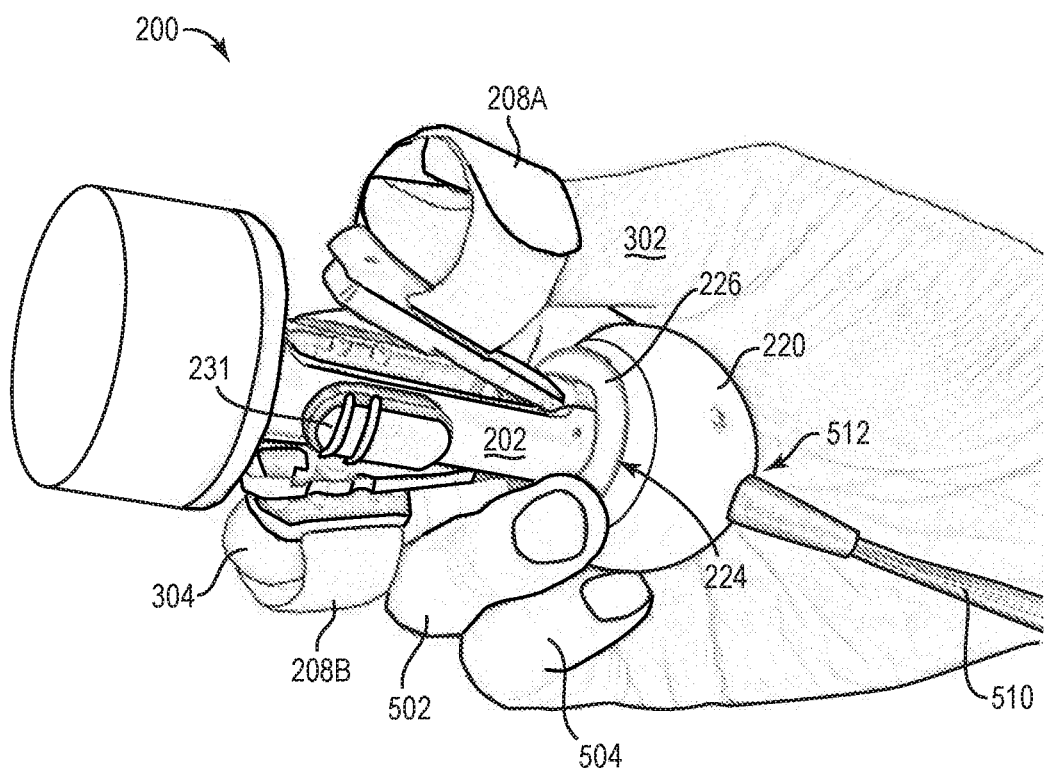
FIG. 5 is another perspective view of the master controller of FIG. 2 being manipulated by a user's hand to activate a switch adjacent to the extension member, according to some implementations.

FIG. 5 is another perspective view of the master hand controller 200 being manipulated by a user's hand to activate a switch adjacent to the extension member, according to some implementations. FIG. 5 shows an example of an underside view of the hand controller and hand positions shown in FIG. 3, or after the user has rotated the hand controller and hand in space.

In this example, the user has used a fourth finger 502 to activate the extension member switch 224 by engaging and moving the ring 226. For example, the second finger 306 of the user (shown in FIG. 3) can continue to engage and activate the switch 230 (shown in FIG. 3) while the ring finger 502 engages and activates the extension member switch 224. In some implementations, the fifth finger 504 can alternately be used to engage the ring 226 to activate the extension member switch 224. A second finger switch 231 can be provided on the opposite side of the control portion 202 to the finger switch 230 shown in FIG. 4. In some examples, the second finger switch 231 can be activated by finger 502 or finger 504, e.g., a finger that is different than the finger 396 that activates the switch 230.

Figure 7:
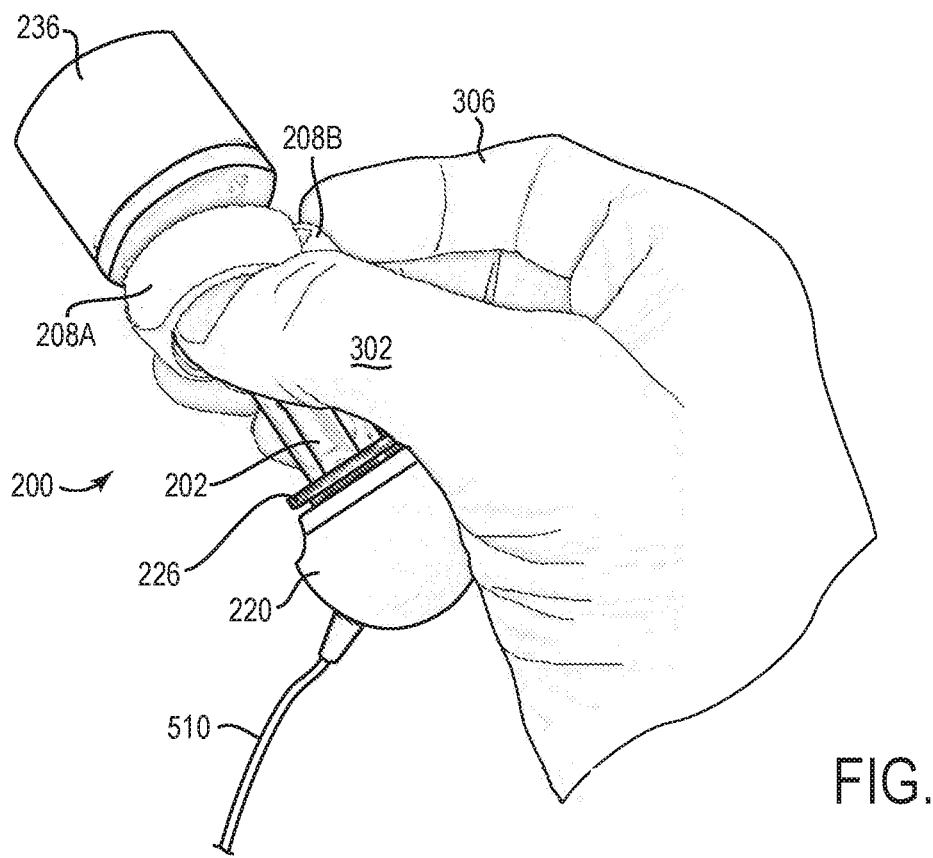
FIG. 7 is a perspective view of the master controller of FIG. 2 being manipulated by a user's hand to a second orientation, according to some implementations.

The example of FIG. 5 also shows an example of a tethered connection (e.g., electrical wire or cable) 510 extending from the extension member 220 at the proximal end of the hand controller. The connection 510 can be connected to a control system as described above and used to communicate electronic signals to and from the hand controller 200. In this example, the user can manipulate the hand controller 200 while the tethered connection 510 extends out the side of the user's hand/palm opposite to the finger side of the palm that engages the extension member 220. Since the extension member 220 may rest in the user's palm, in some implementations the tethered connection 510 can extend from the control body or extension member at least partially radially from the central longitudinal axis 203, instead of extending out of the center of the extension member 220 along axis 203. This may allow the tethered connection 510 to avoid interfering with the palm. One example is shown in FIG. 7. In implementations allowing rotation of the extension member 220, the point 512 where the tethered connection meets the extension member 220 can be rotated about the central axis 203, allowing the tethered connection to extend out of the controller 200 at a point that is adjustable by the user about axis 203, e.g., to accommodate the current grip of the user on the controller.

In some implementations, such a proximal end tether can provide increased security due to the weight of the tether being closer to the user's hand and palm, and may allow less collisions with the tether since it is out of the path of motion of the hand controller 200 in space, unlike in some implementations of a tether extending from the distal end of the hand controller 200. In implementations in which the extension member 220 can rotate with respect to the central portion 202, this rotation allows the tethered connection 510 to maintain its position extending away from the palm of the user's hand while the central portion 202 and grips 204 are rotated in space. In some implementations, a tethered connection can be connected and extended from the distal end of the hand controller, as described above.

Figure 6:
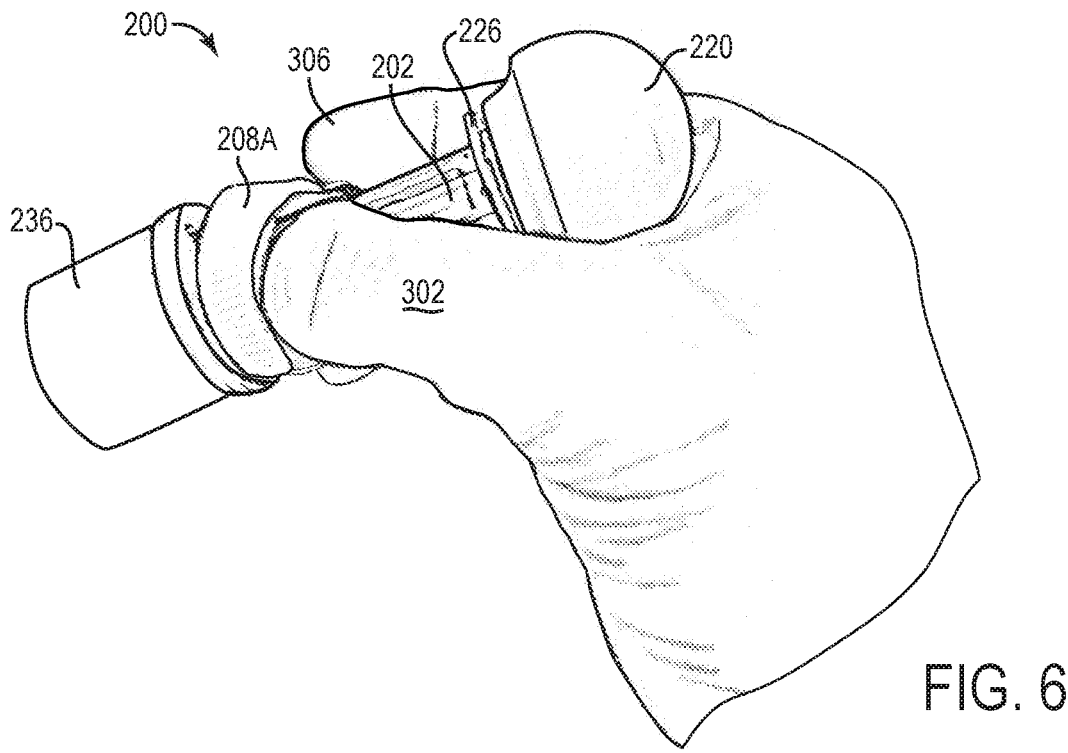
FIG. 6 is a perspective view of the master controller of FIG. 2 being manipulated by a user's hand to a first orientation, according to some implementations

FIG. 6 is a perspective view of the master hand controller 200 being manipulated by a user's hand to a first orientation, according to some implementations. FIG. 6 shows an example of a view of the hand controller and hand positions after the user has moved the extension member 220 of the hand controller 200 out of the space adjacent to or contacting the palm of the hand.

In this example, the user has rotated the control body 201, including central portion 202 and extension member 220, using the thumb (first finger) 302 and third finger 306 of the hand on the grips 206. The lengths of the central portion 202 and extension member 220 are sufficiently short to allow the extension member 220 to pivot out of the space near the palm and in a direction through the space between thumb 302 and second finger 306, e.g., past or adjacent to the webbing between the thumb and second finger (forefinger) of the hand, such that the extension member 220 is no longer in the space adjacent to the palm and is no longer contacting the palm. In some examples, the length of the hand controller 200 thus allows the user to freely manipulate the orientation of the hand controller 200 in space to control functions of a slave device (e.g., teleoperated slave device 102 of FIG. 1) without severe restriction on those orientations due to interference with the user's hand.

FIG. 7 is a perspective view of the master hand controller 200 being manipulated by a user's hand to a second orientation, according to some implementations. FIG. 7 shows an example of a view of the hand controller and hand positions after the user has moved the extension member 220 of the hand controller 200 out of the space adjacent to or contacting the palm of the hand. In this example, the extension member 200 has been moved in a direction different than and/or opposite to the direction of movement of the controller 200 shown in FIG. 6, e.g., in the direction away from the space between the first finger 302 and the second finger 306. In this example, the user has rotated the central portion 202 and extension member 220 using the thumb (first finger) 302 and third finger 306 of the hand on the grips 206.

The lengths of the central portion 202 and extension member 220 are sufficiently short to allow the extension member 220 to pivot out of the space near the palm such that the extension member 220 is no longer in the space adjacent to the palm and is no longer contacting the palm. In some examples, the length of the hand controller 200 thus allows the user to freely manipulate the orientation of the hand controller 200 in space to control functions of a slave device (e.g., teleoperated slave device 102 of FIG. 1) without severe restriction on those orientations due to interference with the user's hand.

The example of FIG. 7 also shows an example of the tethered connection (e.g., electrical cable) 510 extending from the extension member 220 as described with reference to FIG. 5. In this example, the user can manipulate the hand controller 200 while the tethered connection 510 extends from the extension member 220 on a side of the extension member that is opposite to the user's palm.

Figure 8:
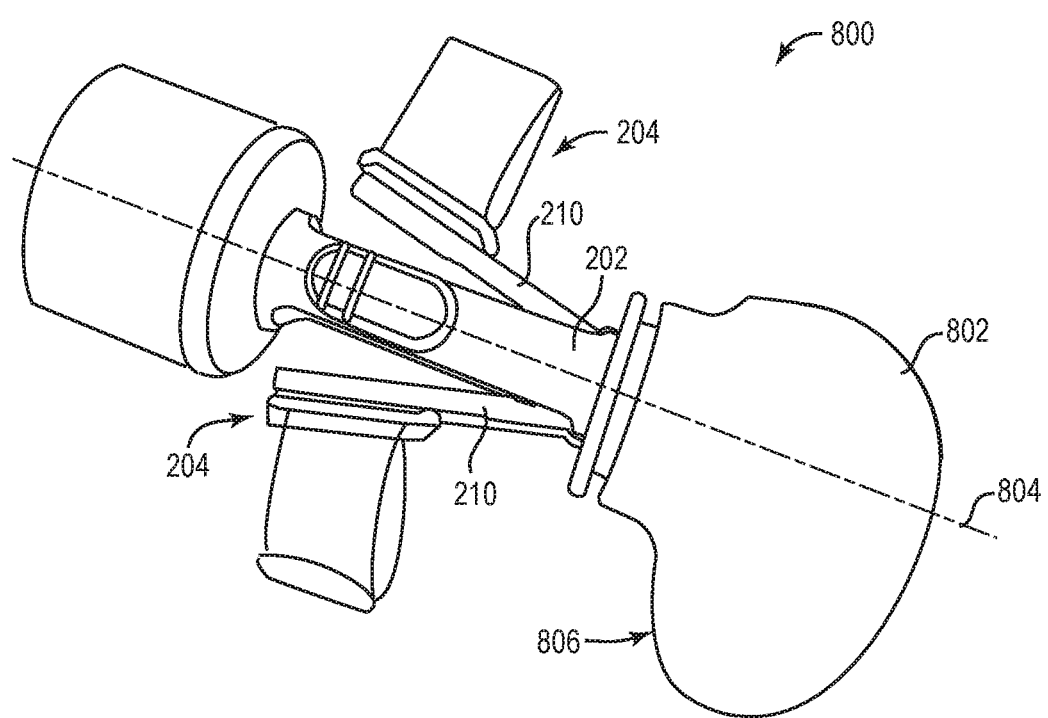
FIG. 8 is a perspective view of another implementation of a master hand controller, according to some implementations.

FIG. 8 is a perspective view of another implementation of a hand controller 800. Hand controller 800 includes many of the same elements described above for controller 200 of FIG. 2 and these elements are numbered identically to FIG. 2.

Hand controller 800 includes an asymmetrical extension member 802. For example, the extension member 802 has a shape that is asymmetric with respect to the longitudinal axis 804 of the control body 201. In this example, the asymmetric shape includes an extended portion 806 that extends asymmetrically to one side of and approximately perpendicularly to the longitudinal axis 804. For example, during operation of the hand controller 800, portion 806 can extend into and/or contact the palm of the user's operating hand, and portion 806 can be receptive to and/or grasped by one or more fingers of the user, e.g., the fourth and/or fifth fingers. The asymmetrical extension member 802 can have a smooth and curved surface that allows it to move easily out of the palm of the operating hand.

Figure 9:
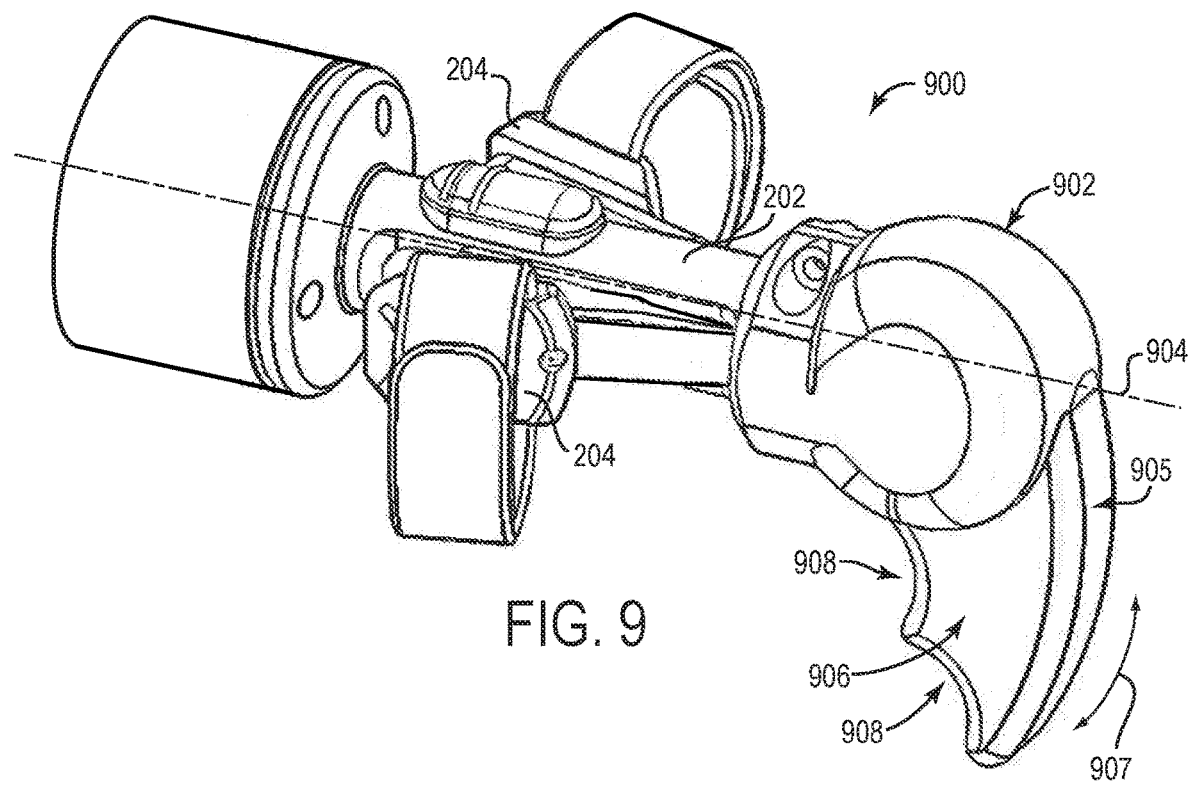
FIG. 9 is a perspective view of another implementation of a master hand controller, according to some implementations.

FIG. 9 is a perspective view of another implementation 900 of a hand controller. Hand controller 900 includes many of the same elements described above for controllers 200 and 800 of FIGS. 2 and 8 and some of these elements are numbered identically. Hand controller 900 includes an asymmetrical extension member 902 rotatably coupled to a central portion 202 of the hand controller 900. For example, the extension member 902 has an asymmetric shape with respect to the longitudinal axis 904 of the central portion 202a. In this example, the asymmetric shape includes a handle portion 906 that extends to one side of and perpendicularly to the axis 904, e.g., a portion of the proximal end extending asymmetrically to one side of the longitudinal axis of the control body. The asymmetrical extension member 902, including handle portion 906, can have a smooth and curved palm-facing surface 905 that allows it to move easily in and out of the palm of the operating hand, e.g., especially in the pitch-angle directions of arrow 907.

The finger grip members 204 can be configured to be receptive to a first finger, second finger, and/or third finger of the hand, and the proximal end, e.g., extension member 902, can be configured to be receptive to a third finger, fourth finger, and/or fifth finger of the hand. For example, during operation of the hand controller 900, the handle portion 906 can be grasped by one or more fingers of the user, e.g., in various configurations: the third, fourth, and fifth fingers; the fourth and fifth fingers; the third and fourth fingers; the third and fifth fingers; the third finger; the fourth finger; or the fifth finger. In some implementations, as shown, the handle portion 906 can include indentations 908 on a side of the handle portion 906 that is, e.g., opposite to the surface 905 contacted by the palm or other hand surfaces. The indentations 908 are spaced to be receptive to and engage one or more fingers of the user's hand operating the hand controller 900, e.g., the fourth and fifth fingers in some examples. In some implementations, indentations, protrusions, or other features can be spaced at various locations of the handle portion 906 in other configurations.

Figure 10:
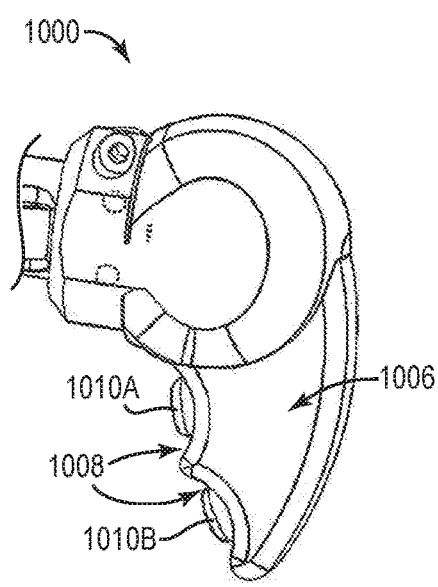
FIG. 10 is a perspective view of another example implementation of an extension member for the master hand controller, according to some implementations.

FIG. 10 is a perspective view of another example implementation of an extension member 1000. Extension member 1000 is an asymmetrical extension member similar to the extension member 902 shown in FIG. 9, including indentations 1008 in handle portion 1006 similar to the indentations 908. Additionally, extension member 1000 includes one or more input controls coupled thereto, which are configured to detect a threshold amount of contact with a finger of the hand. In this example, each input control is a button 1010A and 1010B (generally referred to as button 1010) provided in an associated indentation 1008 of the handle portion 1006. For example, one of the user's fingers can engage an indentation 1008 and activate (e.g., press) the button 1010 provided in that indentation. In some examples, the fourth finger of the operating hand can engage button 1010A, and the fifth finger can engage button 1010B. In some implementations, each button 1010 can provide a different control signal when activated by the user. Any number of buttons 1010 or other types of switches or controls can be provided on the extension member 1000 to enable user activation of various control signals. For example, a larger button or activation switch can be provided on the grip portion 1006 that can be squeezed or pressed by the user's fingers and/or palm. In some implementations, an input control can be provided on the side(s) of the extension member 1000 and/or handle portion 1006 and can be activated by a finger of the hand, e.g., the first and third fingers.

Figure 11:
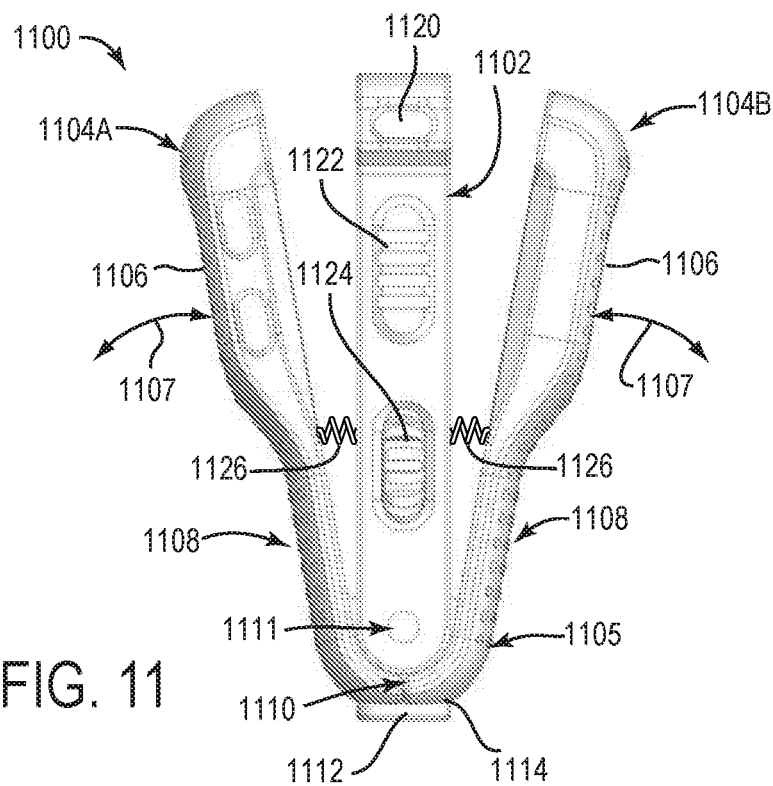
FIG. 11 is a top plan view of another example implementation of a master hand controller, according to some implementations.
Figure 12:
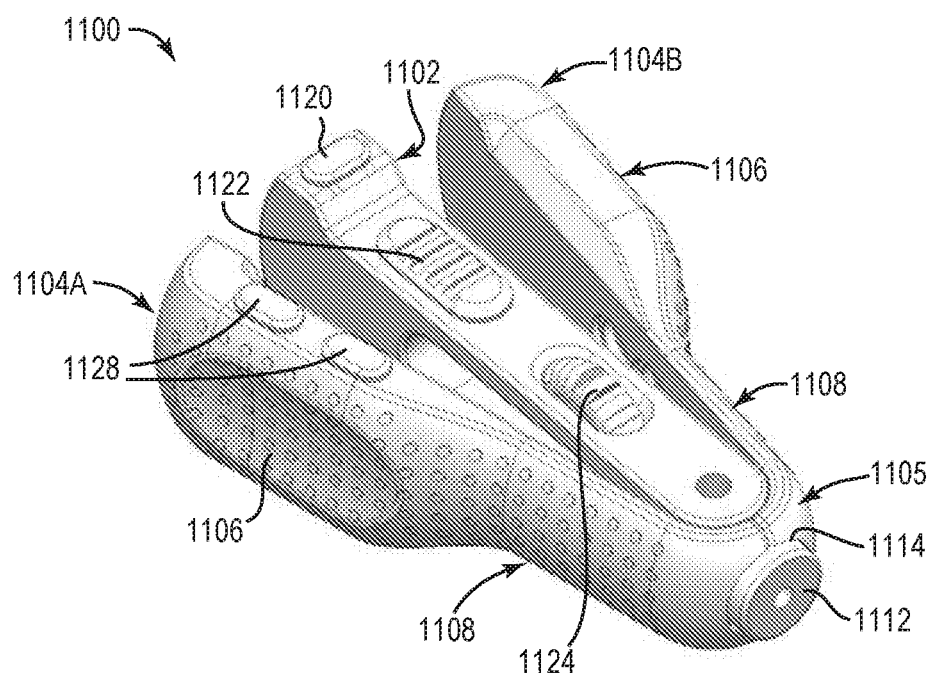
FIG. 12 is a perspective view of another example implementation of a master hand controller, according to some implementations.

FIG. 11 is a top plan view and FIG. 12 is a perspective view of another example implementation of a hand controller 1100 that can be used similarly to hand controller 200. Controller 1100 includes a central portion 1102 and grip portions 1104, including grip portion 1104A and grip portion 1104B, generally referred to as 1104. In this example, the grip portions 1104 are provided as pieces that are connected to the central portion 1102 at a location 1111 (or at a location 1110 in some implementations). For example, the control body 1102 can include a protrusion 1112 that extends through an aperture 1114 in the grip portions 1104 at the location 1110. In some implementations, the grip portions 1104 can be formed as a single piece or unitary grip member in which the grip portions are joined, where the grip portions 1104 can move relative to each other based on flex in the unitary grip member, e.g., at or near location 1110.

In this implementation, grip portions 1104 include respective grips 1106 and grip members 1108. For example, grips 1106 can be end portions of the grip portions 1104 that have features configured to receive and engage a user's fingers. In this example, indentations are provided as grips 1106 near the distal ends of the grip members 1108, where the indentations are shaped to fit the touching side (pads) of a user's fingers.

Furthermore, in some implementations, the surface of the grip portions 1104 can be textured to engage the user's fingers with more friction and grip than a smoother surface. For example, a grid or other pattern of small, raised circular bumps are provided over the outer surfaces of grips portions 1104, e.g., opposite to the central portion 1102, as shown in FIGS. 11 and 12. Other sizes, shapes, and patterns of raised bumps or other texture features can be used in various implementations (e.g., long ridges, random or irregular patterns, etc.).

In some implementations, the two grip portions 1104 are not connected to each other at location 1110 and are configured to move with respect to each other about a pivot point at location 1111 when pinched and released by fingers of the user. Grip portions 1104A and 1104B can pivot relative to central portion 1102 as indicated by arrows 1107 in FIG. 11. For example, the grip portions 1104 can be moved toward each other using a pinch motion with fingers of the user engaging the grips 1106. In some implementations, a spring 1126 (or actuator) can be coupled between grip member 1104A and central portion body 1102, and/or a spring 1126 (or actuator) can be coupled between grip member 1104B and central portion 1102. Springs 1126 provide a restoring or spring force on the grip members 1104, which biases the grip members 1104 toward a neutral position shown in FIGS. 11 and 12. In some implementations, a unitary grip portion that includes both grip portions 1104A and 1104B can be a flexure, e.g., providing flex at or near location 1110. Such a unitary flexure can provide a restoring force on the grip members 1104 in addition to or instead of a restoring force provided by springs 1126.

Hand controller 1100 includes multiple input controls in the example of FIG. 11. For example, a button 1120 is positioned on the top side at the distal end of the central portion 1102. This button can be pressed to send a control signal to the control system to activate an associated function of the connected system, e.g., teleoperated surgical system 100 of FIG. 1. A slider switch 1122 is similar to the finger switch 230 described with respect to FIG. 2. A control wheel 1124 is positioned, in this example, on the control body 1102 closer to the proximal end of the control body, but can be positioned in other locations of the hand controller. The control wheel 1124 can be rotated by a user's finger to provide a user-adjusted control signal based on the position or motion of the control wheel 1124 that can be used to cause adjustment of parameters or functions of the teleoperated system 100, scroll displayed information on a display screen, etc.

Input controls can also be positioned on either or both of the grip members 1104. For example, two buttons 1128 are shown positioned on the top surface of grip member 1104A. In some examples, these buttons can be reached and activated by a user's finger (e.g., thumb) that presses on the grip 1106 of the grip member 1104A. This thumb activation can provide a more stable reaction force on the hand controller 1100 compared to using a different finger to activate the buttons. Alternatively, a different finger can select the buttons. A variety of other types of controls can be positioned in these and other areas of the hand controller 1100, e.g., trackballs, joysticks, dials, etc.

In some examples, particular control functions of a teleoperated slave device can be mapped to the activation of the finger controls of hand controller 1100. Such control functions can be re-mapped to other functions in some implementations. Such functions can include, for example, a swap function for button 1130 allowing control of a first telemanipulator arm or instrument to be swapped to a second arm or instrument; a camera function and/or clutch function for slider switch 1122 (e.g., one function for one switch position, the other function for the other switch position); a user interface scroll function for the control wheel 112, allowing scrolling of displayed interface elements; and energy output for slave instruments mapped to the buttons 1128.

An extension member can be coupled to the hand controller 1100 in some implementations. In some examples, the extension member can be coupled at the protrusion 1112 at the proximal end of the hand controller 1100. For example, the extension member can be any of the implementations of extension members described with reference to FIGS. 2-10. Further examples of an extension member that can be used with hand controller 1100 or other hand controller implementations herein are described below.

Figure 13:
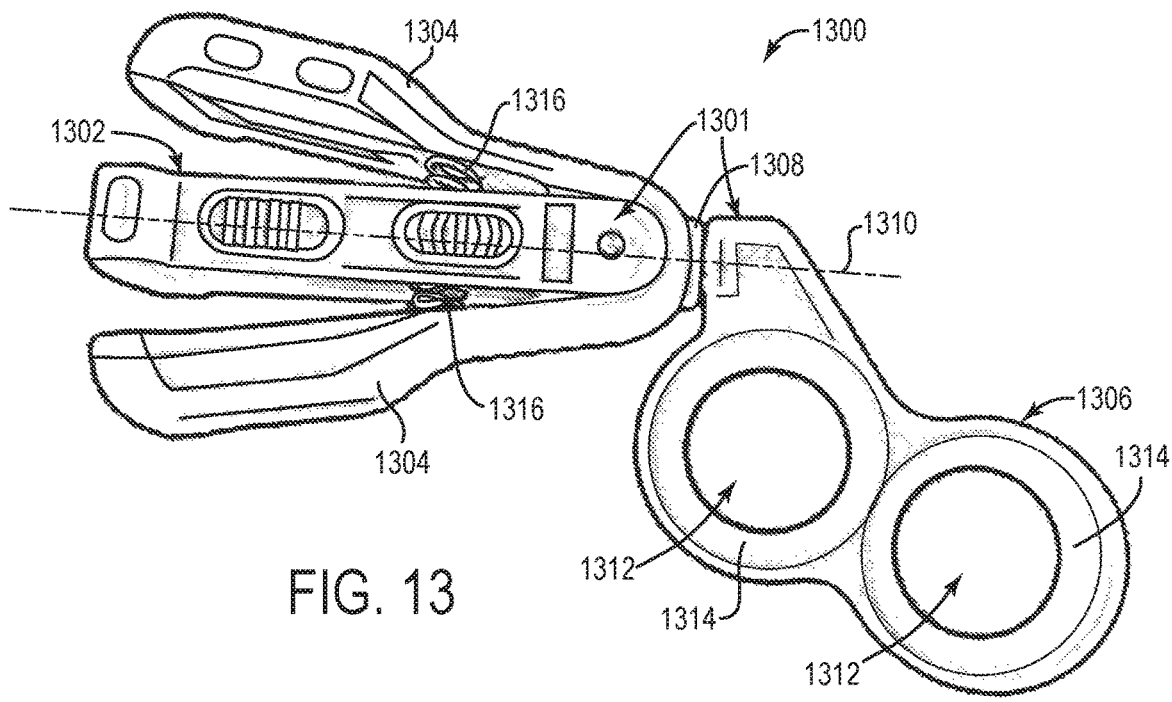
FIG. 13 is a perspective view of another example of a master hand controller that includes an extension member having one or more finger apertures, according to some implementations.

FIG. 13 is a perspective view of another example of a hand controller 1300 that can be used similarly to hand controller 200 and includes an extension member having one or more finger apertures (e.g., finger rings). In this example, a portion of the hand controller 1300 that includes the central portion 1302 and grip members 1304 is similar to the corresponding portion including components 1102 and 1104 in the hand controller 1100 of FIG. 11. In some implementations, other components can be used for the central portion 1302 and grip members 1304, e.g., similarly as in other implementations described above.

A control body 1301 includes the central portion 1302 and extension member 1306. Extension member 1306 can be coupled to the central portion 1302 and/or grip members 1304. In some examples, extension member 1306 can be rotatably coupled to a protrusion 1308 at the proximal end of the central portion 1302 and/or grip members 1304, which can be a protrusion of the central portion 1302 through a unitary piece that includes grip members 1304 similarly as described above for hand controller 1100 of FIG. 11. In some implementations, protrusion 1308 can be included as part of the unitary member of grip members 1304 or other component of the hand controller 1300. The extension member 1306 can be coupled to the central portion 1302 and/or grip members 1304 by a rotary coupling, such that extension member 1306 can be rotated about axis 1310 with respect to the central portion 1302 and grip members 1304. In some implementations, the extension member 1306 can be rigidly coupled to the central portion 1302 and/or grip members 1304.

In some implementations, the extension member 1306 can be coupled to the central portion 1302 and/or grip members 1304 by a rotary coupling that includes two magnets. The magnets on the coupled portions can be attached to each other using magnetic force. Other types of couplings can be used in other implementations. In some examples, the coupling can be spherical as described below with respect to FIG. 15. In another example, the coupling can include two rotary couplings and a link between and connecting these rotary couplings, e.g., similar to a universal joint or a gimbal. In another example, the coupling can allow translation of the extension member 1306 with respect to the central portion 1302 and grip members 1304, e.g., in-out movement, such as an elongated coupling member inserted within a receiving coupling member like a sheath. In another example, the coupling can include a flexible connecting portion, e.g., like a trunk or rope, allowing the extension member motion with respect to the central portion 1302 as the flexible connecting portion bends. In further examples, the coupling can be detachable to allow the extension portion 1306 to be attached and removed from the central portion 1302 and/or grip portions 1304. For example, attracting magnets can be located on the extension member 1306 and the protrusion 1508.

The finger grip members 1304 can be configured to be receptive to a first finger, second finger, or third finger of the hand, and the proximal end, e.g., extension member 1306, can be configured to be receptive to a fourth finger and/or fifth finger of the hand. In this example, extension member 1306 includes one or more finger apertures 1312 which can receive fingers of the user, and in some implementations are formed by finger rings 1314 in or coupled to the extension member 1306. In this example, the finger apertures 1312 are positioned in the extension member 1306 to receive the last two fingers of the user's hand while the first two fingers and thumb of the hand manipulate the grip members 1304 and central portion 1302. For example, such apertures 1312 can cause the hand controller 1300 to be engaged by the hand of the user and allow the user's hand to grasp the hand controller 1300 more effectively, e.g., by reducing the possibility of inadvertent releases, slips, or drops of the hand controller 1300 by the user. In this example, each aperture 1312 can receive one finger of the user's hand. In some implementations, each of one or more of the finger apertures 1312 can be made large enough to receive two or more fingers of the hand.

In some implementations, partial finger rings can be provided, e.g., such that a portion of the user's finger is enclosed by the ring and not the entire finger (e.g., a curved extension 1414 as described below). In some implementations or uses, the user can grasp the outside of the extension member 1306 without inserting fingers in one or more of the apertures 1312 to, e.g., allow greater range of motion (e.g., fingertip motion) of the controller for particular tasks. In some implementations, one or more input controls can be provided on the extension member 1306 (and/or other extension members 1406 and 1506), e.g., which are accessible to fingers that have been inserted in apertures 1312 during user of the hand controller.

In some implementations, a connection between the central portion 1302/grip members 1304 and the extension member 1306 can be a direct connection (e.g., no rotary or other mechanical coupling), where the connector can be made of a flexible material. The flexibility of such a connection can be used to allow respective movement between the central portion/grip members and the extension member, e.g., without use of a mechanical coupling.

In some implementations, the extension member 1306 (and other extension member implementations described herein) can be made of a flexible material, e.g., a foam rubber material, plastic material, or other material allowing flexure and/or compression. This can allow respective movement between central portion 1302/grip members 1304 and the extension member 1306 as described above. Furthermore, the flexibility of such an extension member 1306 can accommodate a variety of finger sizes, and may allow the extension member to cling to or otherwise engage the fingers of the hand to provide additional grasping security for the hand controller 1300.

Figure 14:
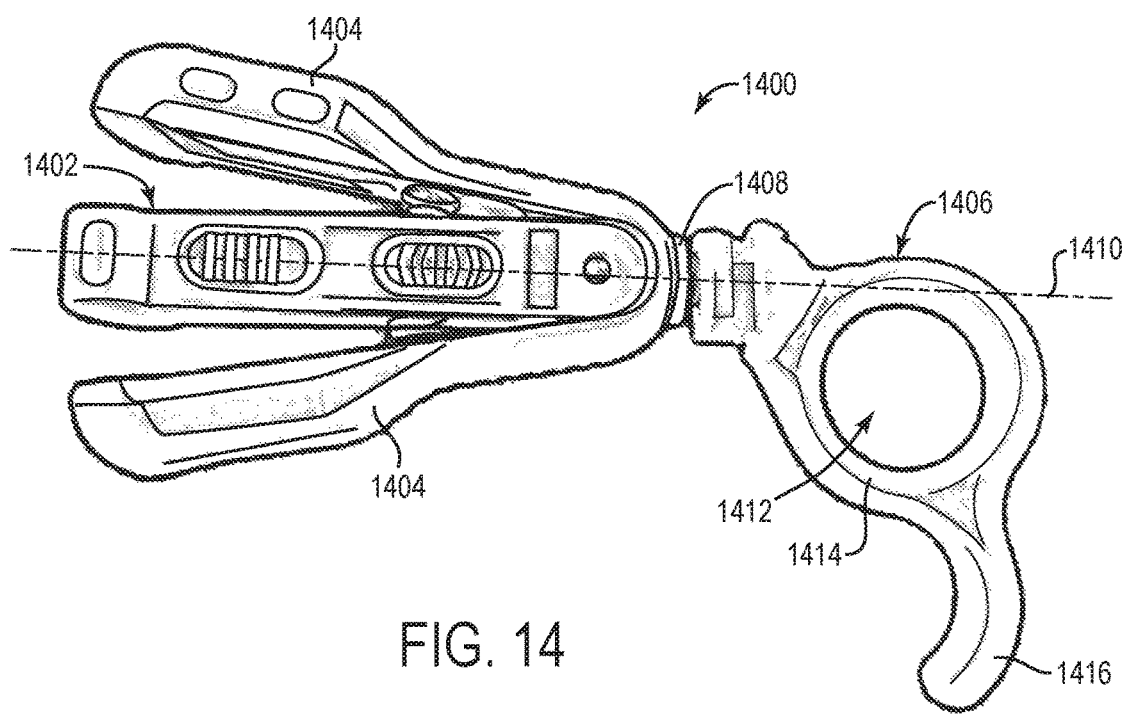
FIG. 14 is a perspective view of another example of a master hand controller that includes an extension member having a finger aperture, according to some implementations.

FIG. 14 illustrates a second example of a hand controller 1400 that includes an extension member having a finger aperture. In this example, a portion of the hand controller 1400 that includes the central portion 1402 and grip members 1404 is similar to the corresponding portion including components 1102 and 1104 in the hand controller 1100 of FIG. 11 and the corresponding portion including components 1302 and 1304 of FIG. 13. In some implementations, other components can be used for the control portion 1402 and grip members 1404, e.g., similarly as in implementations described above.

A control body includes the central portion 1402 and extension member 1406. Extension member 1406 is coupled to the central portion 1402 and/or grip members 1404 similarly as extension member 1306 of FIG. 13. For example, extension member 1406 can be rotatably coupled to a protrusion 1408, e.g., by a rotary coupling, such that extension member 1406 can be rotated about axis 1410 with respect to the central portion 1402 and grip members 1404. In some implementations, the extension member 1406 can be coupled to the central portion 1402 and/or grip members 1404 by a rotary coupling that includes two magnets, or by another type of rotary coupling, e.g., similar to the examples described above for FIG. 13.

Extension member 1406 includes a single finger aperture 1412 which can receive a finger of the user similarly as described for extension member 1306 of FIG. 3. In some implementations, the aperture is formed by a finger ring 1414 in or coupled to the extension member 1406. In this example, the finger aperture 1412 is positioned in the extension member 1406 to receive the ring finger of the user's hand while the first two fingers and thumb of the hand manipulate the grip members 1404 and central portion 1402. A curved extension 1416 can be extended from one side of the extension member 1406, e.g., approximately in a direction perpendicular to the extension member rotary axis 1410 and curving a part of the circumference to form a second aperture similar to the second aperture 1512 shown in FIG. 13. The curved extension 1416 can be contacted or cradled by, e.g., the user's fifth finger, next to the fourth finger that is positioned within the aperture 1412.

Other shapes and configurations of the extension 1416 can be provided in other implementations. In some implementations, the finger aperture 1412 can be made large enough to receive two or more fingers of the hand. For example, aperture 1412 and curved extension 1416 can allow the hand controller to engage the hand of the user and allow the user's hand to grasp the hand controller 1400 more effectively, e.g., by reducing the possibility of inadvertent releases or drops of the hand controller by the user.

Figure 15:
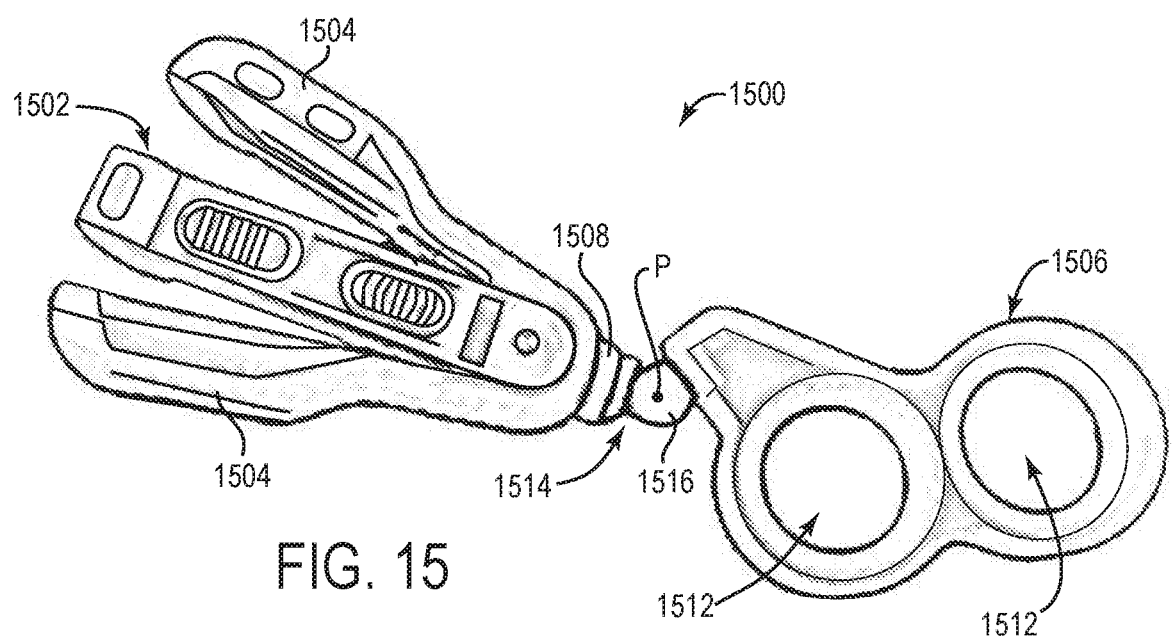
FIG. 15 is a perspective view of another example of a master hand controller that includes an extension member having one or more finger apertures, according to some implementations.

FIG. 15 illustrates a second example of a hand controller 1500 that can be used similarly to hand controller 200 and that includes an extension member having one or more finger apertures. In this example, a control portion of the hand controller 1500 that includes the central portion 1502 and grip members 1504 is similar to the corresponding components in the hand controllers 1100, 1300, and 1400 described above. Other components can be used for the central portion 1502 and grip members 1504, e.g., similarly as in implementations described above.

Extension member 1506 is coupled to the control body 1502 and/or grip members 1504, e.g., coupled to a protrusion 1508 of the central portion 1502 and/or grip members 1504. In this example, extension member 1506 is coupled by a spherical joint (e.g., ball joint) 1514 that allows the extension member 1506 to be rotated about a point P of the joint 1514. For example, spherical joint 1514 can use magnets, a mechanical connection, or other connection to provide the coupling. The spherical joint 1514 couples the extension member 1506 to the protrusion 1508. In some examples, a ball 1516 of the spherical joint 1514 is rigidly attached to the extension member 1506 and is rotationally coupled to the protrusion 1508, e.g., magnetically coupled to a magnet rigidly attached to the central portion 1502. In some implementations, the opposite configuration can be used.

The spherical joint 1514 allows more directions of motion of the extension member 1506 compared to the extension member 1306 of FIG. 13, and allows flexibility in positioning the hand controller 1500 in the user's hand during manipulation of the hand controller 1500. In some implementations, spherical joint 1514 can be provided with friction to cause the central portion 1502 and grip members 1504 to stay in their positions when the fingers of the user release their contact with the grip members 1504, or the spherical joint can provide a looser coupling. In some implementations, the ball joint 1514 can be detachable to allow the extension portion 1506 to be attached and removed from the central portion 1502 and/or grip portions 1504. For example, attracting magnets can be located on the ball joint 1516 and the protrusion 1508.

In other implementations, spherical joint 1514 can be a ball joint having a bearing stud and a socket in which the bearing stud can rotate. For example, the bearing stud can be coupled to either the extension member 1506 or the central portion 1502 in various implementations.

Extension member 1506 includes two finger apertures 1512 in the example shown, which can receive the user's finger for stability and security, and are similar to the apertures 1312 as described above for extension member 1306 of FIG. 13. In other implementations, a single finger aperture 1512 and/or a curved extension can be provided for extension member 1506, similarly to the extension member 1406 of FIG. 14. In some implementations, each of one or more of the finger apertures 1512 can be made large enough to receive two or more fingers of the hand.

Figure 16:
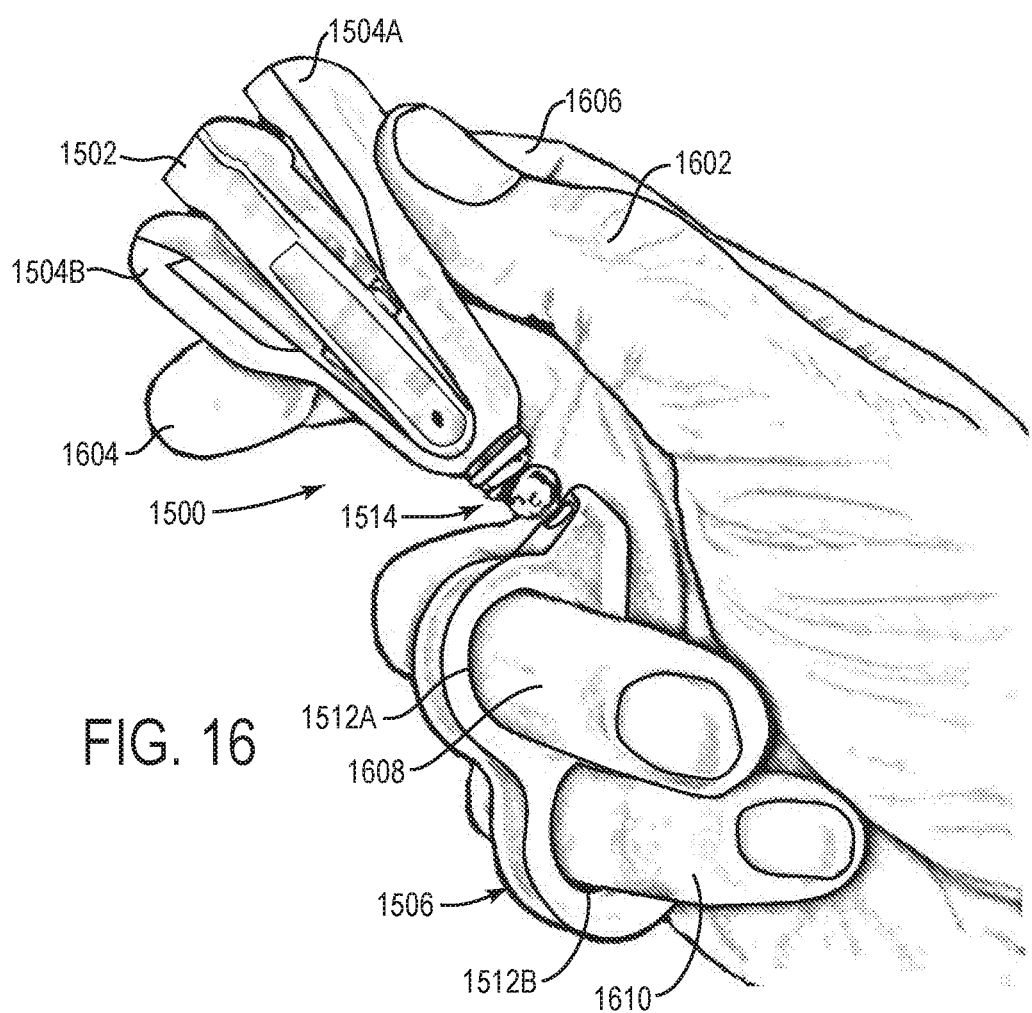
FIG. 16 is a perspective view of a user's hand holding and operating a master hand controller of FIG. 15, according to some implementations.

FIG. 16 is a perspective view of a user's hand holding and operating a hand controller 1500 described with respect to FIG. 15. Hand controller 1500 is held such that the user's first finger 1602 is engaging grip member 1504A, the user's third finger 1604 is engaging grip member 1504B, and the user's second finger 1606 is free to engage or activate input controls on the hand controller 1500 (input controls not shown in FIG. 16). In the position shown, the user's fourth finger 1608 is inserted in the finger aperture 1512A of the extension member 1506, and the user's fifth finger 1610 is inserted in the finger aperture 1512B of the extension member 1506.

In operation, the users fingers 1602 and 1604 can push or pinch the grip members 1504 toward the central portion 1502 to a closed position, and the grip members 1504 can be restored to their open position away from the central portion 1502 via a restoring force, e.g., provided by the flexure of the grip member unitary member, and/or a spring or other actuator. The extension member 1506 can be swiveled or pivoted in a variety of directions or degrees of freedom with respect to the central portion 1502 and grip members 1504 using the spherical joint 1514.

In other implementations, the hand controller 1300 of FIG. 3 and the hand controller 1400 of FIG. 4 can be similarly grasped and operated by the hand of a user.

Figure 17:
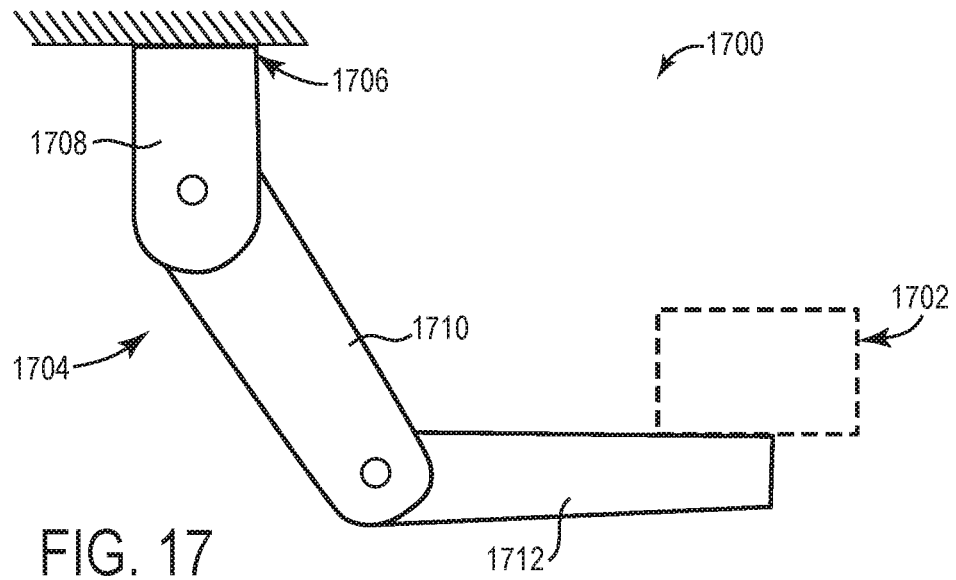
FIG. 17 is a schematic illustration of view of an example controller system that is mechanically grounded.

FIG. 17 is a schematic diagram of an example controller system 1700 that is mechanically grounded, and which can be used with one or more features described herein for a master controller. Controller system 1700 includes a control portion 1702 that can be engaged by a user's hand. The control portion 1702 includes a hand controller portion that can include one or more features described herein, as well as one or more mechanisms. Some examples of control portion 1702 are described in greater detail below with respect to FIG. 18.

Control portion 1702 is coupled to a serial kinematic chain 1704. The proximal end 1706 of the chain 1702 is mechanically grounded. In this example, the kinematic chain 1706 includes three members 1708, 1710, and 1712 that are rotatably coupled to one or more other members of the chain 1706 by rotational couplings having rotational axes. For example, member 1708 is mechanically grounded at a first end 1706 of member 1708 and is rotatably coupled to member 1710 at a second end of member 1708. Member 1710 is rotatably coupled to member 1708 at a first end of member 1710 and rotatably coupled to member 1712 at a second end of member 1710. Member 1712 is rotatably coupled to member 1710 at a first end of member 1712 and coupled (e.g., rotatably coupled) to control portion 1702 at a second end of the member 1712. The rotational axes of the chain 1704 can be sensed and/or driven by sensors and/or actuators. Some implementations can provide additional actuated and/or sensed motion of the kinematic chain, e.g., about axes extending lengthwise through one or more members 1708, 1710, and 1712.

Figure 18:
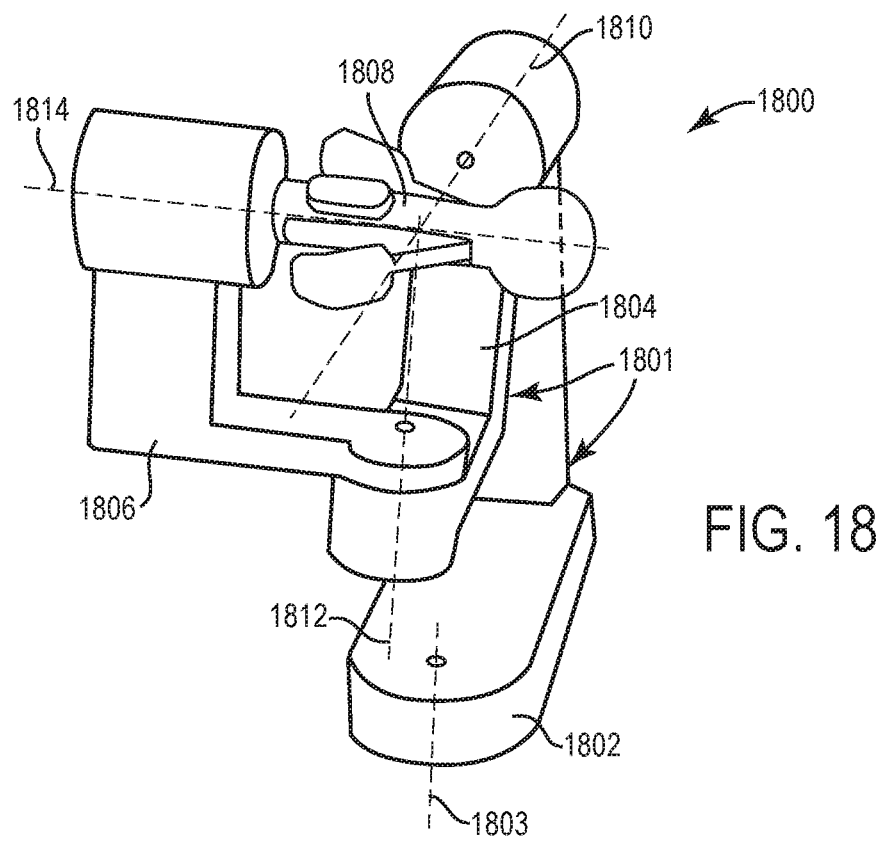
FIG. 18 is a perspective view of an example control portion that is mechanically grounded and can be engaged by a user.

FIG. 18 is a perspective view of an example control portion 1800 that is mechanically grounded and can be engaged by a user. In some examples, control portion 1800 can be the control portion 1702 of the controller system 1700 of FIG. 17. In some implementations, control portion 1800 can be coupled to a different kinematic chain or other structure that is mechanically grounded.

In this example, control portion 1800 includes members of a serial kinematic chain 1801 that includes three members 1802, 1804, and 1806 that are rotatably coupled to one or more other members of the chain 1801 by rotational couplings having rotational axes.

Control portion 1800 can be coupled by a rotational coupling at a first end of member 1802 to the second end of member 1712 of the kinematic chain 1704, allowing rotation about axis 1803 between members 1712 and 1802. Member 1802 is rotatably coupled to member 1804 at a second end of member 1802. Member 1804 is rotatably coupled to member 1802 at a first end of member 1804 and rotatably coupled to member 1806 at a second end of member 1804. Member 1806 is rotatably coupled to member 1804 at a first end of member 1806 and coupled (e.g., rotatably coupled) to a hand controller portion 1808 at a second end of the member 1806. The rotational axes of the chain 1801 can be sensed and/or driven by sensors and actuators.

Hand controller portion 1808 can include features which can be contacted by a user, e.g., a hand of a user. For example, a handle, extension member, grips, switches, and/or other features described herein, e.g., with respect to FIGS. 2-16, can be provided on hand controller portion 1808.

In some implementations, the hand controller portion 1808 is coupled at a distal end of a serial kinematic chain that includes members 1806, 1804, 1802, 1712, 1710, and 1708, with the proximal end 1706 of the chain mechanically grounded. This provides a stable platform for the use of the hand controller portion 1808.

In some implementations, the kinematic chain 1801 forms a gimbal mechanism that allows the hand controller portion 1808 to be rotated about the rotational axes of the chain 1801, e.g., axes 1803, 1810, 1812, and 1814. Hand controller portion 1808 can also be translated in at least three linear degrees of freedom allowed by the kinematic chain formed by kinematic chains 1704 and 1801.

Various kinematic chains, linkages, gimbal mechanisms, flexible structures, or combinations of two or more of these can be used with the mechanically grounded hand controller in various implementations to provide one or more degrees of freedom to the hand controller. Some further examples of linkages and/or gimbal mechanisms that can be used with hand controller portion 1808 are described in U.S. Pat. No. 6,714,839 B2, incorporated herein by reference.

Figure 19:
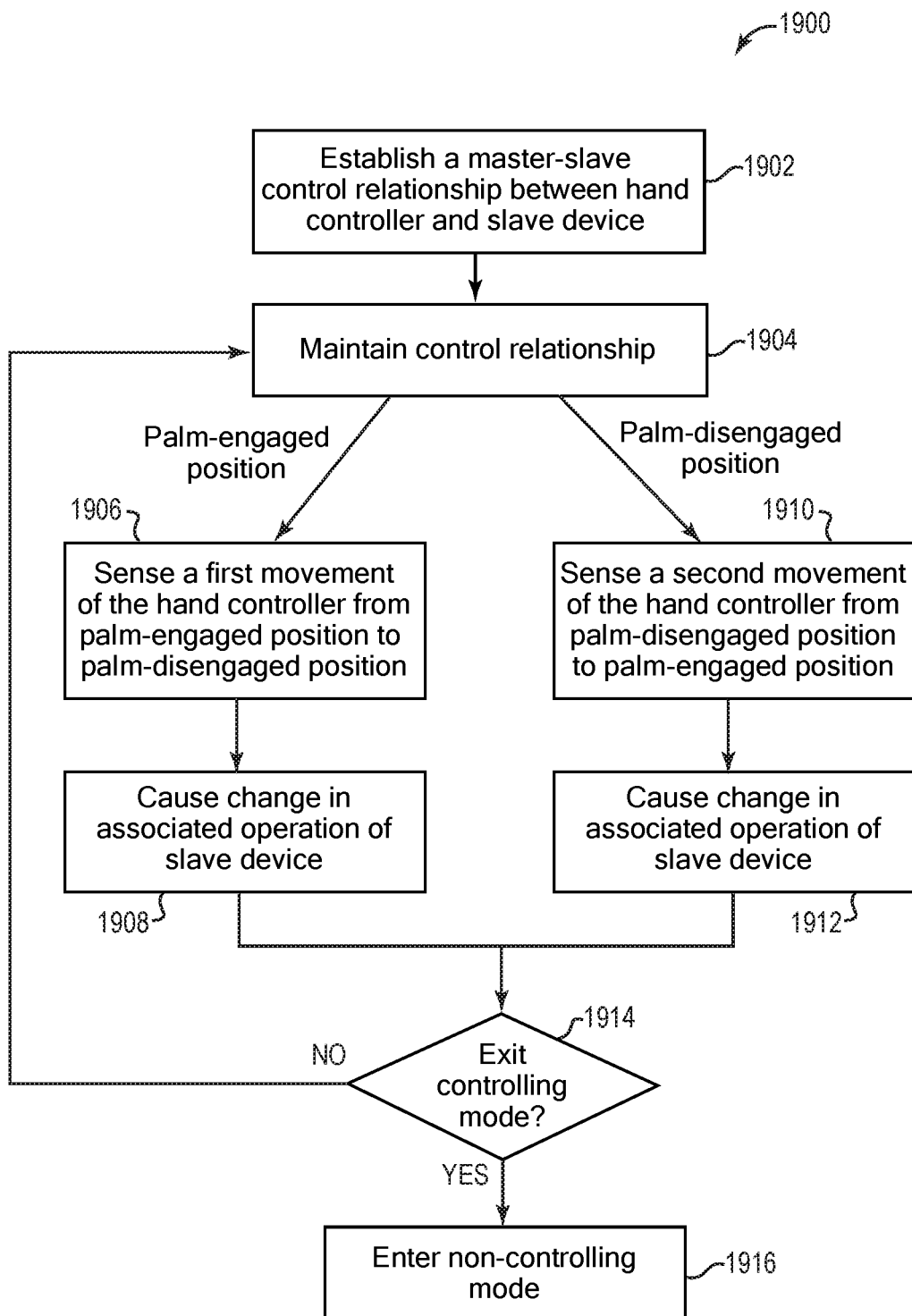
FIG. 19 is a flow diagram illustrating an example method for employing a hand controller including one or more features described herein, according to some implementations.

FIG. 19 is a flow diagram illustrating an example method 1900 for employing a master hand controller including one or more features described herein, according to some implementations. Method 1900 can, for example, be used with an example teleoperated system or other control system in which the hand controller is a master controller that controls a slave device. For example, in some implementations, the hand controller is a mechanically ungrounded master controller, e.g., master control device 122 of FIG. 1, and method 1900 can be performed by a control circuit component of the master control device 122, e.g., performed by control system 150. In some examples, the control circuit can include one or more processors, e.g., microprocessors or other control circuits, some examples of which are described below with reference to FIG. 21. A single master controller is referred to in method 1900 for explanatory purposes. The master controller can be, for example, any of the controller implementations described herein. Multiple master controllers can be similarly processed as described in method 1900. Other implementations can use a controller having one or more features described herein with other types of systems, e.g., non-teleoperated systems, a virtual environment (e.g., medical simulation) having no physical slave device and/or no physical subject interacting with a physical slave device, etc.

In block 1902, a master-slave control relationship is established between the ungrounded hand controller and a slave device, such as a slave surgical device or instrument in some examples. In some implementations, this can be entering a controlling mode of the hand controller. For example, this control relationship can be established in response to receiving a control signal from the hand controller or a different component of the system that indicates that the hand controller is to enter a controlling mode (or following mode). In the controlling mode (during the established control relationship), particular manipulations of the hand controller cause changes in associated state(s) or activations of associated functions of the controlled slave device. For example, motion of the hand controller in space causes corresponding motion of a controlled instrument of the slave device, and/or activation of one or more controls on the hand controller causes activation of a function of the controlled instrument (e.g., application of energy to a target site).

In block 1904, the control relationship established in block 1902 is maintained. Two control options for the hand controller that are described in this example method are moving the hand controller from a palm-engaged position to a palm-disengaged position, and moving the hand controller from a palm-disengaged position to a palm-engaged position. These control options can be combined with various other motions of the hand controller in space. Other control options for the hand controller as described throughout this description.

If the hand controller is in a palm-engaged position, then the method continues to block 1906. In the palm-engaged position, an extension member at the proximal end of the hand controller, such as extension member 220 of FIG. 2, is engaged by (e.g., grounded to) the user's palm, e.g., is contacting, cradled, or cupped by the palm of the user's hand.

In block 1906, a first movement of the hand controller is sensed, from the palm-engaged position to a palm-disengaged position. The sensing can be performed using any of a variety of sensing systems as described above. The palm disengaged position is a position of the hand controller in which the extension member is not contacted or cradled by the palm of the user's hand. For example, this position can be approximately lateral to the palm-engaged position after a rotation of the extension member resulting from the user pivoting the hand controller with fingertip control, e.g., around a pivot point at or near the grips of the hand controller. A palm-disengaged position can be to either side of the palm-engaged position, for example. Some examples of a disengaged position are described above with reference to FIGS. 6 and 7. The method continues to block 1908.

In block 1908, a change is caused in associated operation of the controlled slave device based on the sensed first movement. For example, the change in operation can be motion of the controlled slave device that corresponds to the first movement of the hand controller. In some examples, a slave instrument can be moved in a corresponding direction and/or a corresponding distance to the first movement in space. In other examples, a change in operation of an instrument end effector is performed, e.g., jaws of a grasping device can be opened or closed in correspondence with the first movement. The method continues to block 1914.

If the hand controller is not in the palm-engaged position in block 1904, the method continues to block 1910. In block 1910, a second movement of the hand controller is sensed, from the palm-disengaged position to a palm-engaged position. This block can be performed similarly to block 1906. The method continues to block 1912.

In block 1912, a change is caused in associated operation of the controlled slave device based on the sensed second movement. In some examples, the change in operation can be motion of the controlled slave device that corresponds to the second movement of the hand controller. In some examples, a slave instrument can be moved in a corresponding direction and/or a corresponding distance to the second movement in space. In other examples, operation of an end effector of a slave instrument can be changed, e.g., jaws of grasping device opened or closed in correspondence with the second movement. The method continues to block 1914.

In block 1914, it is checked whether the controlling mode is exited. For example, controlling mode can be exited in response to the user activating an input control (e.g., a button) of the hand controller, removing one or more fingers from the grips of the controller, a voice command, other user input, etc. In other examples, controlling mode can be exited in response to a procedure (e.g., surgical procedure) being completed, a condition in the procedure (e.g., an unsafe movement or position of the slave device occurs), etc.

If controlling mode is not exited, the method returns to block 1904 to maintain the control relationship between the hand controller and the slave device. If controlling mode is exited, then in block 1916 the master-slave control relationship is removed or ended, and a non-controlling mode can be entered by the hand controller and control system in which manipulations of the hand controller do not control functions or operations of the slave device. In some implementations, non-controlling mode removes physical or motion control of the slave device or other particular functions, while some functions of the slave device may still be controlled by the hand controller (e.g., input to a displayed user interface of the slave device, causing output of audio, etc.). The controlling mode can be again entered similarly as described for block 1902.

The blocks and operations described in the methods disclosed herein can be performed in a different order than shown and/or simultaneously (partially or completely) with other blocks and operations, where appropriate. Some blocks and operations can be performed for one portion of data and later performed again, e.g., for another portion of data. Not all of the described blocks and operations need be performed in various implementations. In some implementations, blocks and operations can be performed multiple times, in a different order, and/or at different times in the methods.

In various implementations, input controls of the hand controller can be manipulated by the user's hand to provide control signals to the control system and/or to the slave device, e.g., at any time during method 1900. As described above, such input controls can include grips and grip members, buttons, wheels, etc.

In some additional examples, input controls can provide control signals to provide input to a displayed user interface, virtual environment, or other display provided by a display device, e.g., a user interface displayed on a display 126 of FIG. 1. In some examples, sliding finger switch 230 (or other input control on the various hand controller implementations) can be a clutch control, where, for example, pulling the switch toward a position toward the proximal end of the hand controller (and/or maintaining the switch at that position) provides a clutch function to enter controlling mode (following mode) with the hand controller. In some implementations, pushing the switch 230 to a position closer to the distal end of the hand controller can exit the hand controller from controlling mode and cause it to enter non-controlling mode, or cause activation of a different function (e.g., camera control mode in which motion of the hand controller controls a camera of the slave device, a user interface mode in which input from the input controls is provided to a displayed user interface, etc.).

Movement and orientation of the hand controller and activation of input controls are sensed by various sensors as described above, and sensor signals are sent to a controller (e.g., control system 150) in response to the sensing. The controller activates one or more selected functions of a plurality of functions provided by a system in communication with the hand controller. For example, a control system 150 or control module can send commands to other system components to activate one or more functions based on the sensor signals received from the hand controller.

The term "function" as used herein can include one or more actions or outputs (including operations or motions) of a controlled slave device, e.g., a surgical slave device. For example, a surgical slave device may include surgical instruments as described above, and a function can include one instrument action or multiple instrument actions (e.g., actions performed serially and/or at least partially in parallel). In some implementations, a function can be a category of actions performed by a surgical instrument. In some examples, a cutting tool such as a knife or a surgical scissors may perform various actions in the category of cutting. In some implementations, the input control activating a function causes one or more actions associated with the activated function to be performed. For example, a cutting function can include one or more actions such as moving a scalpel to create an incision in a surgical site with a straight cut. Alternatively, the cutting function can include actions such as snipping a blood vessel with a surgical scissors, to be cauterized.

Surgical instruments may include cutting tools, grasping tools, cauterizing tools, irrigation tools, suction tools, absorbing tools, etc. In some implementations, the hand controller (or control system) outputs teleoperation control signals based on the sensor signals to control functions including movements of the surgical instruments, and/or mechanical arms holding the surgical instruments, in communication with the hand controller. Various functions can be associated with such controlled instruments or tools, including irrigation (injecting a liquid into or onto a surgical site or other location), suction (removing of such liquid), clutch (disengage control of slave device manipulator arms, e.g., to allow master controllers to be repositioned without such control), turning on or off a camera (capture or record a scene at a physical location such as a surgical site), outputting energy by a cutting tool to cut or seal biological tissue, etc.

In some implementations, an input control may be activated by the user (e.g., button pressed) to cause a control signal to be sent and cause activation of a function associated with the input control. In some implementations, the input control is operative to maintain output of the control signal to the system while the input control continues to be activated based on continued user input at the input control (e.g., a button is required to continue to be pressed in order to maintain output of the control signal to the system). In some implementations, the maintained output of the control signal causes the selected function to continue being activated by the system. For example, electrical energy may be applied to perform a coagulate function while an input control button is pressed. In some implementations, an audio signal may be output by the control system to indicate the energy is being applied. In another example, a clutch function and non-controlling mode may be activated and maintained while an input control button is pressed and maintained in pressed state, while controlling mode is active while the button is released. In another example, camera control may be activated as an input control button is continually pressed to allow the hand controller to control camera position and/or orientation, and the button is released (deactivated) to return the hand controller back to controlling the position and/or grip of a surgical grasping instrument and not control the camera position and orientation.

In some implementations, an input control on the hand controller can be used as a toggle to enter or exit control modes. For example, the input control button is pressed and released once to enter camera mode, and is again pressed and released to return to instrument control mode. In another example, the input control can be used to toggle (swap or switch) the arm or instrument being controlled by a hand controller, e.g., switch control to a different manipulator arm on a slave device. In some implementations, the input control may be used to deselect and/or deactivate a function, e.g. using a deselect toggle. In some implementations, the input control can be used as a trigger to initiate a sequence of functions or actions, e.g., a staple sequence of a stapler instrument.

In some implementations, a user interface (UI) and/or status readout can be displayed on one or more display devices of the system (e.g., display screens, virtual reality or augmented reality headsets or goggles, etc.). The user interface can display information related to operation of the hand controller.

In some implementations, actuators can be included in the hand controller to actively output forces on the hand controller, e.g., motors, voice coils, etc. In some examples, such forces can be used to alert the user to particular conditions of the hand controller, of the procedure, etc. For example, a vibration alert can be output by one or more actuators of the hand controller (e.g., a motor rotating an oscillating element), where a vibration force is transmitted to the hand operating the hand controller. In some examples, the vibration alert can be output in response to collisions that have occurred between controlled slave instruments and other objects, in response to a controlled instrument or arm reaching a limit to motion, as a safety alert when using a cutting or energy-outputting instrument, etc. In some implementations, distinct vibration signatures can be provided in association with different respective alerts (e.g., different vibration frequencies and/or amplitudes). Other types of forces can be used for such alerts in some implementations, e.g., single pulses of force, etc.

In some implementations, output such as haptic feedback on the hand controller (e.g., on the grip members 204) and/or visual displays on a display device can be provided by the system to assist user operation of the teleoperated surgical system. For example, a user interface may display warnings and/or error feedback on a display device, and/or audio output can be provided to indicates such warnings or errors.

Such feedback can indicate functions that are potentially dangerous to a patient, and/or that a function to be activated is not appropriate (e.g., according to steps of a stored predetermined procedure) based on previous hand controller movement or previous function(s) activated.

In various implementations, other types of computer-assisted teleoperated systems can be used with one or more hand controller features described herein, in addition to surgical systems. Such teleoperated systems can include controlled slave devices of various forms. For example, submersibles, bomb disposal units, industrial applications, applications in hostile environments and worksites (e.g., due to weather, temperature, pressure, radiation, or other conditions), general robotics applications, and/or remote-control applications (e.g., remote controlled vehicle or device with a first-person view), may utilize teleoperated systems that include slave devices for sensory transmission (conveyed visual, auditory, etc. experience), manipulation of work pieces or other physical tasks, etc., and may use mechanically grounded and/or ungrounded master controllers to remotely control the slave devices. Any such teleoperated systems can be used with the various hand controller features described herein.

FIG. 20 is a diagrammatic illustration of an example teleoperated slave device and patient site 2000 for an example teleoperated surgical system, which can be used with one or more features disclosed herein according to some implementations.

A manipulator slave device 2002 can be controlled by one or more master controllers of a master control device. For example, one or more master control devices 122 as shown in FIG. 1 can be used to control slave device 2002, or one or more hand controller described herein. During a surgical procedure, the slave device can be positioned close to an operating table and patient (or simulated patient) for surgery, where it can remain stationary until a particular surgical procedure or stage of a procedure is completed. Slave device 2002 can include one or more arm assemblies 2014, 2016, and 2018. In some examples, each of these arm assemblies may include a surgical instrument 2024, 2026, and 2028, respectively. Each surgical instrument can include a surgical end effector, e.g., for treating tissue of the patient. An arm assembly 2020 (or other arm assembly 2014, 2016, or 2018) can be configured to hold an image capturing device, e.g., an endoscope 2030, camera, or the like, which can capture images depicting a surgical site or portion thereof. The endoscope can be in communication with to one or more display devices and transmit images to the display devices, such as display device 126 of FIG. 1, a display device 2032 coupled to the slave device, and/or other display devices.

In this example, the arm assemblies may be caused to move and articulate the surgical instruments in response to manipulation of the master controller(s). This enables the user to direct surgical procedures at internal surgical sites through minimally invasive surgical apertures. For example, one or more actuators coupled to the arm assemblies can output force to cause links or other portions of the arm assemblies to move in particular degrees of freedom in response to control signals provided by the master controllers. The master controllers can be used within a room (e.g., an operating room) that also houses the slave device and worksite (e.g., within or outside a sterile surgical field close to an operating table), or can be positioned more remotely from the slave device, e.g., at a different room, building, or other location than the slave device.

Some implementations of the teleoperated system can provide different modes of operation. In some examples, in a non-controlling mode (e.g., safe mode) of the teleoperated system, the controlled motion of manipulator slave device 2002 is disconnected from the master controllers of the workstation in a disconnected configuration, such that movement and other manipulation of the master controls does not cause motion of the manipulator slave device. In a controlling mode of the teleoperated system (e.g., following mode), the motion of the manipulator slave device can be controlled by the master controllers such that movement and other manipulation of the master controllers causes motion of the manipulator slave device, e.g., during a surgical procedure.

In some implementations, the teleoperated surgical system can include a support on which a user, e.g., an operator such as a surgeon, can rest his or her forearms while gripping two grounded master controllers. For example, the master controllers can be positioned in a workspace disposed inwardly toward a patient, beyond the support.

Features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Non-teleoperated systems can also use features described herein.

In some implementations, a controlled slave manipulator device can be a virtual representation of device, e.g., presented in a graphical simulation provided by a computing device coupled to the teleoperated system 2000. For example, a user can manipulate hand master controllers and foot controller(s) to control a displayed representation of an end effector in virtual space of the simulation and control virtual functions of the representation (or other virtual instruments) similarly as if the end effector were a physical object coupled to a physical slave device. Such environments can be used for training surgeons in the use of the hand controllers, in some implementations. In some examples, the user can use or manipulate a master controller to control a proxy visual (e.g., a virtual instrument displayed in a virtual displayed environment, and/or a virtual camera or physical camera included on the slave device or other device), and to control teleoperated surgical arms 2014, 2016, 2018, and 2020.

Figure 21:
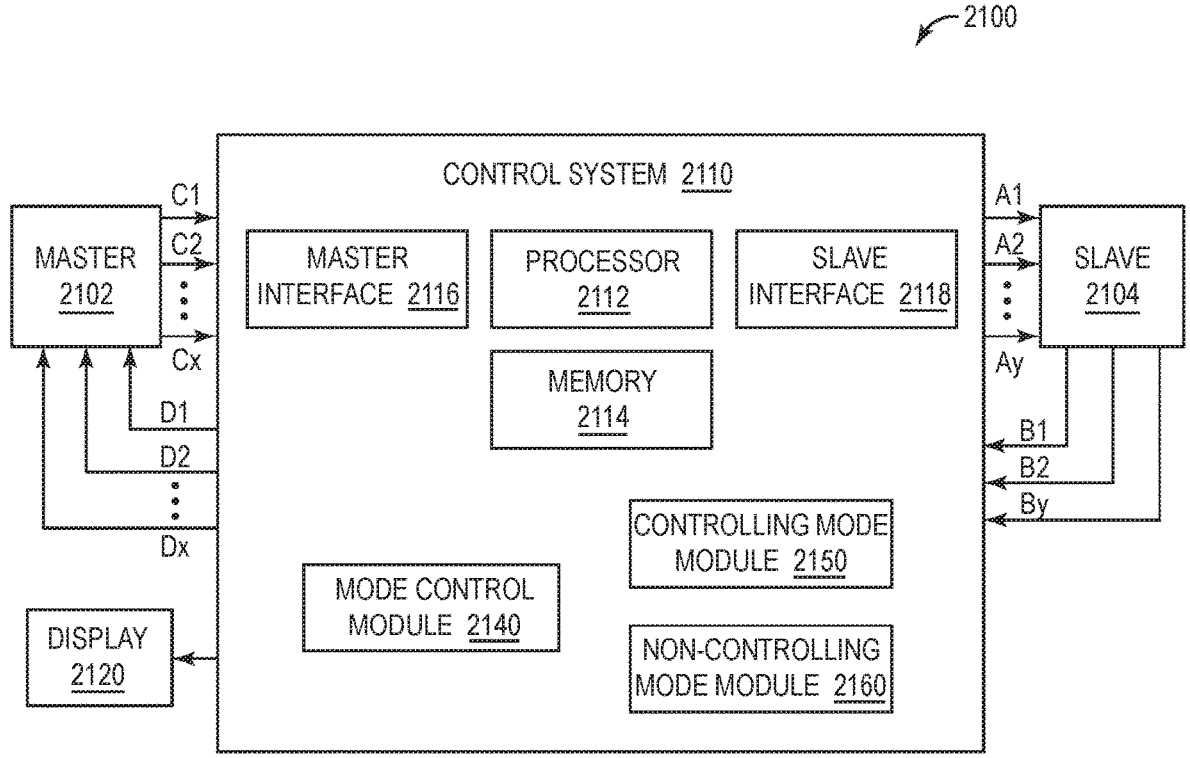
FIG. 21 is a block diagram of an example master-slave system, which can be used for one or more implementations described herein.

FIG. 21 is a block diagram of an example master-slave system 2100, which can be used for one or more implementations described herein. As shown, system 2100 includes a master device 2102 that a user may manipulate in order to control a slave device 2104 in communication with the master device 2102. More generally, master device block 2102 can include one or more of various types of devices providing one or more hand controllers that can be physically manipulated by a user. For example, master device 2102 can include a system of one or more master controllers such as one or more hand controllers (e.g., master control devices 122 or various other hand controllers described herein).

Master device 2102 generates control signals C1 to Cx indicating positions and orientations, states, and/or changes of one or more controllers in their degrees of freedom. For example, the master device 2102 can generate control signals indicating selection of input controls such as physical buttons, hand controller states, and other manipulations of the hand controller by the user.

A control system 2110 can be included in the master device 2102, in the slave device 2104, or in a separate device, e.g., an intermediary device communicatively connected between master device 2102 and slave device 2104. In some implementations, the control system 2110 can be distributed among multiple of these devices. Control system 2110 receives control signals C1 to Cx and generates actuation signals A1 to Ay, which are sent to slave device 2104. Control system 2110 can also receive sensor signals B1 to By from the slave device 2104 that indicate positions and orientations, states, and/or changes of various slave components (e.g., manipulator arm elements). Control system 2110 can include general components such as a processor 2112, memory 2114, and interface hardware 2116 and 2118 such as a master interface and a slave interface for communication with master device 2102 and slave device 2104, respectively. Processor 2112 can execute program code and control basic operations of the system 2100, and can include one or more processors of various types, including microprocessors, application specific integrated circuits (ASICs), and other electronic circuits. Memory 2114 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control system 2110, e.g., one or more displays 2120.

In this example, control system 2110 includes a mode control module 2140, a controlling mode module 2150, and a non-controlling mode module 2160. Other implementations can use other modules, e.g., a force output control module, sensor input signal module, etc. As used herein, the term "module" can refer to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware. In some implementations, the modules 2140, 2150, and 2160 can be implemented using the processor 2112 and memory 2114, e.g., program instructions stored in memory 2114 and/or other memory or storage devices connected to control system 2110.

Mode control module 2140 can detect when a user initiates a controlling mode and a non-controlling mode of the system, e.g., by user selection of controls, sensing a presence of a user using a master controller, sensing required manipulation of a master controller, etc. The mode control module can set the controlling mode or a non-controlling mode of the control system 2110 based on one or more control signals C1 to Cx. For example, mode control module 2140 may activate controlling mode operation if user detection module detects that a user is in proper position for use of the master controller(s) and that signals (e.g., one or more signals C1 to Cx) indicate the user has contacted the master controller(s). The mode control module 2140 may disable controlling mode if no user touch is detected on the master controller(s) and/or if a user is not in proper position for use of the master controller(s). For example, the mode control module 2140 can inform control system 710 or send information directly to controlling mode module 2150 to prevent the controlling mode module 2150 from generating actuation signals A1 to An that move slave device 2104.

In some implementations, controlling mode module 2150 may be used to control a controlling mode of control system 2110. Controlling mode module 2150 can receive control signals C1 to Cx and can generate actuation signals A1 to Ay that control actuators of the slave device 2104 and cause it to follow the movement of master device 2102, e.g., so that the movements of slave device 2104 correspond to a mapping of the movements of master device 2102. Controlling mode module 2150 can be implemented using conventional techniques.

In some implementations, controlling mode module 2150 can also be used to control forces on the controller(s) of the master device 2102 as described herein, e.g., forces output on one or more components of the master controllers, e.g., hand grip members, using one or more control signals D1 to Dx output to actuator(s) used to apply forces to the components. For example, one or more of control signals D1 to Dx can be output to one or more actuators configured to output forces to one or more hand controllers, actuators configured to output forces on links coupled to a master controller (if it is a mechanically grounded master controller), etc. In some examples, control signals D1 to Dx can be used to provide haptic feedback, gravity compensation, etc.

In some implementations, a non-controlling mode module 2160 may be used to control a non-controlling mode of system 2100. In the non-controlling mode, user manipulations of master device 2102 have no effect on the movement of one or more components of slave 2104. In some examples, non-controlling mode may be used when a portion of slave 2104, e.g., a slave arm assembly, is not being controlled by master device 2102, but rather is floating in space and may be manually moved. For non-controlling mode, non-controlling mode module 2160 may allow actuator systems in the slave 2104 to be freewheeling or may generate actuation signals A1 to An, for example, to allow motors in an arm to support the expected weight of the arm against gravity, where brakes in the arm are not engaged and permit manual movement of the arm. For example, in a medical procedure, non-controlling mode may allow a surgical side assistant to easily manipulate and reposition an arm or other slave component relative to a patient or directly make some other clinically appropriate adjustment of the arm or slave component.

In some implementations, non-controlling mode can include one or more other operating modes of the control system 2110. For example, a non-controlling mode can be a selection mode in which movement of the master controller in one or more of its degrees of freedom and/or selection of controls of the master controller can control selection of displayed options, e.g., in a graphical user interface displayed by display 2120 and/or other display device. A viewing mode can allow movement of the master controller(s) to control a display provided from imaging devices (e.g., cameras), or movement of imaging devices, that may not be included in the slave device 2104. Control signals C1 to Cx can be used by the non-controlling mode module 2160 to control such elements (e.g., cursor, views, etc.) and control signals D1 to Dx can be determined by the non-controlling mode module to cause output of forces on the master controller(s) during such non-controlling modes, e.g., to indicate to the user interactions or events occurring during such modes.

Implementations described herein may be implemented, at least in part, by computer program instructions or code, which can be executed on a computer. For example, the code may be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general-purpose processors, graphics processors, Application Specific Integrated Circuits (ASICs), and the like.

Implementations provide various benefits. For example, a hand controller described herein can be provided with control over operation and functions of a slave device, such as a surgical slave device. Described features such as the length, shape, grips, input controls, and other features of an extension member of the hand controller provide additional security and reduced fatigue in operating the hand controller to reduce incidences of inadvertent slippage or dropping of the hand controller by the user during operation. For example, the extension member is provided at a length and with a surface allowing the proximal end of the controller to be readily grasped and contacted by the palm of the user's hand, yet allows the controller to have large fingertip range of motion to provide accurate and precise control over slave instruments. The features increasing grasping security and reducing fatigue are of high importance in procedures such as medical procedures in which controlled surgical instruments operate on a live patient. Due to the fatigue that surgeons may experience over an extended surgical operation using master controllers, the described controller features are useful in performing teleoperated surgical procedures and other procedures or tasks.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the scope of the present disclosure. Accordingly, many modifications may be made by one of ordinary skill in the art without departing from the scope of the appended claims.

What is claimed is:

1. A control device comprising:
   a control body having a longitudinal axis;
   a thumb grip member coupled to the control body;
   a finger grip member coupled to the control body;
   a ring element coupled to the control body and surrounding the longitudinal axis of the control body; and
   an activation sensor coupled to the control body,
   wherein the ring element moves in a linear translation along the longitudinal axis with reference to the control body and independently of the thumb grip member and the finger grip member,
   wherein the activation sensor is configured to detect the linear translation of the ring element and is activated based on the linear translation of the ring element, and
   wherein the ring element is configured to be selectively engaged by a first finger of a hand of a user while the thumb grip member is engaged with a thumb of the hand and the finger grip member is engaged with a second finger of the hand.

2. The control device of claim 1, wherein the control body includes a proximal end and a length, wherein the longitudinal axis extends through the proximal end, and wherein the length of the control body is sufficient to engage the proximal end of the control body in a palm of the hand of the user while the thumb grip member is engaged with the thumb of the hand and the finger grip member is engaged with the second finger of the hand.

3. The control device of claim 2, wherein:
   The control body is configured to allow the proximal end of the control body to be moved between the thumb of the hand and an index finger of the hand while the hand engages the thumb grip member with the thumb of the hand and the finger grip member with the second finger of the hand, and
   the control body is configured to allow the proximal end of the control body to be selectively engaged by and disengaged from the palm of the hand while the hand engages the thumb grip member with the thumb of the hand and the finger grip member with the second finger of the hand.

4. The control device of claim 1, wherein the activation sensor is configured to output a signal that is based on a predefined position of the ring element in a linear degree of freedom along the longitudinal axis, and wherein the predefined position of the ring element is one of two or more different available predefined positions of the ring element.

5. The control device of claim 1, wherein:
   the control device further comprises a spring return element coupled to the ring element; and
   the spring return element urges the ring element to translate along the longitudinal axis of the control body.

6. The control device of claim 1, wherein the control device is a surgical system control device configured to provide control signals to a surgical teleoperated system.

7. The control device of claim 1, wherein the control device comprises a sensor configured to detect at least one of a position or an orientation of the control device in a working environment of the control device.

8. The control device of claim 1, wherein:
   the thumb grip member is rotatably coupled to the control body; and
   the finger grip member is rotatably coupled to the control body.

9. The control device of claim 8, wherein the thumb grip member and the finger grip member are rotatable toward or away from each other.

10. The control device of claim 1, wherein the control device is mechanically ungrounded.

11. The control device of claim 1, wherein the control body includes a proximal end, wherein the proximal end has an axisymmetric shape with respect to the longitudinal axis of the control body.

12. The control device of claim 1, wherein the control body includes a proximal end, wherein the proximal end of the control body comprises an extension member that extends asymmetrically to one side of the longitudinal axis of the control body.

13. The control device of claim 1, wherein:
the control body includes a proximal end, the proximal end of the control body comprises an extension member;
the control device further comprises a tethered connection coupled to the extension member at a connection point;
the extension member is rotatable about the longitudinal axis of the control body independently of the control body, the thumb grip member, and the finger grip member such that the connection point rotates about the longitudinal axis of the control body;
the tethered connection extends from the extension member radially with reference to the longitudinal axis of the control body; and
the tethered connection couples the control body to a control system.

14. The control device of claim 1, wherein:
the control body includes a proximal end,
the control device further comprises an input control coupled to the proximal end of the control body;
the input control is configured to detect a threshold amount of contact with another finger of the hand; and
the input control is coupled to a portion of the proximal end of the control body that extends asymmetrically to one side of the longitudinal axis.

15. The control device of claim 1, wherein:
the thumb grip member comprises a thumb contact surface;
the finger grip member comprises a finger contact surface;
the control device further comprises a distal weighted element and a proximal weighted element;
the control body comprises a proximal end and a distal end opposite the proximal end along the longitudinal axis;
the distal weighted element is positioned at the distal end of the control body;
the proximal weighted element is positioned at the proximal end of the control body; and
the distal weighted element and the proximal weighted element are weighted to provide a center of gravity of the control device between the finger contact surface and the thumb contact surface.

16. A control system comprising:
a control device, a control unit in communication with the control device, and a controlled unit in communication with the control device;
wherein the control device comprises a control body having a longitudinal axis, a thumb grip member coupled to the control body, a finger grip member coupled to the control body, a ring element coupled to the control body and surrounding the longitudinal axis of the control body, and an activation sensor coupled to the control body;
wherein the control body comprises the longitudinal axis;
wherein the ring element moves in a linear translation along the longitudinal axis with reference to the control body and independently of the thumb grip member and the finger grip member;
wherein the activation sensor is configured to detect the linear translation of the ring element and is activated based on the linear translation of the ring element;
wherein the ring element is configured to be selectively engaged by a first finger of a hand of a user while the thumb grip member is engaged with a thumb of the hand and the finger grip member is engaged with a second finger of the hand;
wherein the control unit is configured to provide control signals to the controlled unit while a control relationship is provided between the control device and the controlled unit; and
wherein the control system is configured to maintain the control relationship while the user moves the control device from a first position to a second position.

17. The control system of claim 16, wherein the activation sensor is configured to output a signal that is based on a predefined position of the ring element in a linear degree of freedom along the longitudinal axis, and wherein the predefined position of the ring element is one of two or more different available predefined positions of the ring element.

18. The control system of claim 16, wherein:
the control device further comprises a spring return element coupled to the ring element; and
the spring return element urges the ring element to translate along the longitudinal axis of the control body.

19. The control system of claim 16, wherein the control device comprises a sensor configured to detect at least one of a position or an orientation of the control device in a working environment of the control device.

20. The control system of claim 16, wherein:
the thumb grip member is rotatably coupled to the control body; and
the finger grip member is rotatably coupled to the control body.

* * * * *